United States Patent [19]
Ames et al.

[11] Patent Number: 6,129,913
[45] Date of Patent: *Oct. 10, 2000

[54] RECOMBINANT IL-5 ANTAGONISTS USEFUL IN TREATMENT OF IL-5 MEDIATED DISORDERS

[75] Inventors: Robert S. Ames, Havertown; Edward Robert Appelbaum, Blue Bell; Irwin M. Chaiken, Gladwyn; Richard M. Cook, Chester Springs; Mitchell Stuart Gross, Wayne, all of Pa.; Stephen Dudley Holmes, Epsom, United Kingdom; Lynette Jane McMillan, Ardmore; Timothy Wayne Theisen, Phoenixville, both of Pa.

[73] Assignees: SmithKline Beecham Corporation, Philadelphia, Pa.; SmithKline Beecham p.l.c., Brentford, United Kingdom

[ * ] Notice: This patent is subject to a terminal disclaimer.

[21] Appl. No.: 08/637,647

[22] PCT Filed: Dec. 22, 1995

[86] PCT No.: PCT/US95/17082

§ 371 Date: Jun. 19, 1997

§ 102(e) Date: Jun. 19, 1997

[87] PCT Pub. No.: WO96/21000

PCT Pub. Date: Jul. 11, 1996

Related U.S. Application Data

[63] Continuation-in-part of application No. 08/470,110, Jun. 6, 1995, Pat. No. 5,693,323, and a continuation-in-part of application No. 08/467,420, Jun. 6, 1995, Pat. No. 5,683,892, which is a continuation-in-part of application No. 08/363,131, Dec. 23, 1994, abandoned, said application No. 08/470,110, is a continuation-in-part of application No. 08/363,131, Dec. 23, 1994, abandoned.

[51] Int. Cl.[7] .......................... A61K 39/395; A61K 39/40; C07K 16/00; C12P 21/08

[52] U.S. Cl. ..................................... 424/130.1; 424/133.1; 424/137.1; 424/141.1; 424/145.1; 424/152.1; 424/158.1; 424/172.1; 530/387.1; 530/387.3; 530/388.23

[58] Field of Search .............................. 424/130.1, 133.1, 424/137.1, 141.1, 145.1, 152.1, 158.1, 172.1; 530/387.1, 387.3, 388.23

[56] References Cited

U.S. PATENT DOCUMENTS

| | | |
|---|---|---|
| 4,980,359 | 12/1990 | Hasspacher et al. . |
| 5,096,704 | 3/1992 | Coffman et al. . |
| 5,585,089 | 12/1996 | Queen et al. . |
| 5,783,184 | 7/1998 | Appelbaum et al. . |
| 5,851,525 | 12/1998 | Ames, Jr. et al. . |

FOREIGN PATENT DOCUMENTS

| | | |
|---|---|---|
| 367596 | 5/1990 | European Pat. Off. . |
| WO 93/16184 | 8/1993 | WIPO . |

OTHER PUBLICATIONS

Collet, et al., "A binary plasmid system for shuffling combinatorial antibody libraries", *Proc. Natl. Acad. Sci. USA*, 89 pp. 10026–10030 (1992).

McNamee et al (Journal of Immunological Methods vol. 141 pp. 81–88), 1991.

Maggio (Enzyme Immunoassay CRC Press Inc. pp. 167–178), 1980.

Menard et al (Annali Dell Istituto Superiore Di Sanita vol. 27(1) pp. 87–89), 1991.

*Primary Examiner*—Albert Navarro
*Attorney, Agent, or Firm*—Kirk Baumeister; William T. King

[57] ABSTRACT

Chimeric, humanized and other IL-5 mAbs, derived from high affinity neutralizing mAbs, pharmaceutical compositions containing same, methods of treatment and diagnostics are provided.

8 Claims, 13 Drawing Sheets

| | | | | | | | | | | | |
|---|---|---|---|---|---|---|---|---|---|---|---|
| 1 | CCT | GGC | CTG | GTG | GCG | CCC | TCA | CAG | AGC | CTG | 30 |
| | Pro | Gly | Leu | Val | Ala | Pro | Ser | Gln | Ser | Leu | |
| 31 | TCC | ATC | ACT | TGC | ACT | GTC | TCT | GGG | TTT | TCA | 60 |
| | Ser | Ile | Thr | Cys | Thr | Val | Ser | Gly | Phe | Ser | |
| 61 | TTA | ACC | AGC | TAT | AGT | GTA | CAC | TGG | GTT | CGC | 90 |
| | Leu | Thr | Ser | Tyr | Ser | Val | His | Trp | Val | Arg | |
| 91 | CAG | CCT | CCA | GGA | AAG | GGT | CTG | GAG | TGG | CTG | 120 |
| | Gln | Pro | Pro | Gly | Lys | Gly | Leu | Glu | Trp | Leu | |
| 121 | GGA | GTA | ATA | TGG | GCT | AGT | GGA | GGC | ACA | GAT | 150 |
| | Gly | Val | Ile | Trp | Ala | Ser | Gly | Gly | Thr | Asp | |
| 151 | TAT | AAT | TCG | GCT | CTC | ATG | TCC | AGA | CTG | AGC | 180 |
| | Tyr | Asn | Ser | Ala | Leu | Met | Ser | Arg | Leu | Ser | |
| 181 | ATC | AGC | AAA | GAC | AAC | TCC | AAG | AGC | CAA | GTT | 210 |
| | Ile | Ser | Lys | Asp | Asn | Ser | Lys | Ser | Gln | Val | |
| 211 | TTC | TTA | AAA | CTG | AAC | AGT | CTG | CAA | ACT | GAT | 240 |
| | Phe | Leu | Lys | Leu | Asn | Ser | Leu | Gln | Thr | Asp | |
| 241 | GAC | ACA | GCC | ATG | TAC | TAC | TGT | GCC | AGA | GAT | 270 |
| | Asp | Thr | Ala | Met | Tyr | Tyr | Cys | Ala | Arg | Asp | |
| 271 | CCC | CCT | TCT | TCC | TTA | CTA | CGG | CTT | GAC | TAC | 300 |
| | Pro | Pro | Ser | Ser | Leu | Leu | Arg | Leu | Asp | Tyr | |
| 301 | TGG | GGC | CAA | GGC | ACC | ACT | CTC | ACA | GTC | TCC | 330 |
| | Trp | Gly | Gln | Gly | Thr | Thr | Leu | Thr | Val | Ser | |
| 331 | TCA | | | | | | | | | | 333 |
| | Ser | | | | | | | | | | |

FIG. 1

| | | | | | | | | | | |
|---|---|---|---|---|---|---|---|---|---|---|
| 1 | TCC | TCC | CTG | AGT | GTG | TCA | GCA | GGA | GAG | AAG | 30 |
| | Ser | Ser | Leu | Ser | Val | Ser | Ala | Gly | Glu | Lys | |
| 31 | GTC | ACT | ATG | AGC | TGC | AAG | TCC | AGT | CAG | AGT | 60 |
| | Val | Thr | Met | Ser | Cys | Lys | Ser | Ser | Gln | Ser | |
| 61 | CTG | TTA | AAC | AGT | GGA | AAT | CAA | AAG | AAC | TAC | 90 |
| | Leu | Leu | Asn | Ser | Gly | Asn | Gln | Lys | Asn | Tyr | |
| 91 | TTG | GCC | TGG | TAC | CAG | CAG | AAA | CCA | GGG | CAG | 120 |
| | Leu | Ala | Trp | Tyr | Gln | Gln | Lys | Pro | Gly | Gln | |
| 121 | CCT | CCT | AAA | CTT | TTG | ATC | TAC | GGG | GCA | TCC | 150 |
| | Pro | Pro | Lys | Leu | Leu | Ile | Tyr | Gly | Ala | Ser | |
| 151 | ACT | AGG | GAA | TCT | GGG | GTC | CCT | GAT | CGC | TTC | 180 |
| | Thr | Arg | Glu | Ser | Gly | Val | Pro | Asp | Arg | Phe | |
| 181 | ACA | GGC | AGT | GGA | TCT | GGA | ACC | GAT | TTC | ACT | 210 |
| | Thr | Gly | Ser | Gly | Ser | Gly | Thr | Asp | Phe | Thr | |
| 211 | CTT | TCC | ATC | AGC | AGT | GTG | CAG | GCT | GAA | GAC | 240 |
| | Leu | Ser | Ile | Ser | Ser | Val | Gln | Ala | Glu | Asp | |
| 241 | CTG | GCA | GTT | TAT | TAC | TGT | CAG | AAT | GTT | CAT | 270 |
| | Leu | Ala | Val | Tyr | Tyr | Cys | Gln | Asn | Val | His | |
| 271 | AGT | TTT | CCA | TTC | ACG | TTC | GGC | TCG | GGG | ACA | 300 |
| | Ser | Phe | Pro | Phe | Thr | Phe | Gly | Ser | Gly | Thr | |
| 301 | GAG | TTG | GAA | ATA | AAA | | | | | | 315 |
| | Glu | Leu | Glu | Ile | Lys | | | | | | |

FIG. 2

| | | | | | | | | | | |
|---|---|---|---|---|---|---|---|---|---|---|
| 1 | CCT Pro | GGC Gly | CTG Leu | GTG Val | GCG Ala | CCC Pro | TCA Ser | CAG Gln | AGC Ser | CTG Leu | 30 |
| 31 | TCC Ser | ATC Ile | ACT Thr | TGC Cys | ACT Thr | GTC Val | TCT Ser | GGG Gly | TTT Phe | TCA Ser | 60 |
| 61 | TTA Leu | ACC Thr | AGT Ser | TAT Tyr | AGT Ser | GTA Val | CAC His | TGG Trp | GTT Val | CGC Arg | 90 |
| 91 | CAG Gln | CCT Pro | CCA Pro | GGA Gly | AAG Lys | GGT Gly | CTG Leu | GAG Glu | TGG Trp | CTG Leu | 120 |
| 121 | GGA Gly | GTA Val | ATA Ile | TGG Trp | GCT Ala | AGT Ser | GGA Gly | GGC Gly | ACA Thr | GAT Asp | 150 |
| 151 | TAT Tyr | AAT Asn | TCG Ser | GCT Ala | CTC Leu | ATG Met | TCC Ser | AGA Arg | CTG Leu | AGC Ser | 180 |
| 181 | ATC Ile | AGC Ser | AAA Lys | GAC Asp | AAC Asn | TCC Ser | AAG Lys | AGC Ser | CAA Gln | GTT Val | 210 |
| 211 | TTC Phe | TTA Leu | AAA Lys | CTG Leu | AAC Asn | AGT Ser | CTG Leu | CGA Arg | ACT Thr | GAT Asp | 240 |
| 241 | GAC Asp | ACA Thr | GCC Ala | ATG Met | TAC Tyr | TAC Tyr | TGT Cys | GCC Ala | AGA Arg | GAT Asp | 270 |
| 271 | CCC Pro | CCT Pro | TCT Ser | TCC Ser | TTA Leu | CTA Leu | CGG Arg | CTT Leu | GAC Asp | TAC Tyr | 300 |
| 301 | TGG Trp | GGC Gly | CAA Gln | GGC Gly | ACC Thr | ACT Thr | CTC Leu | ACA Thr | GTC Val | TCC Ser | 330 |
| 331 | TCA Ser | 333 | | | | | | | | | |

FIG. 3

| | | | | | | | | | | | |
|---|---|---|---|---|---|---|---|---|---|---|---|
|1|TCC|TCC|CTG|AGT|GTG|TCA|GCA|GGA|GAG|AAG|30|
| |Ser|Ser|Leu|Ser|Val|Ser|Ala|Gly|Glu|Lys| |
|31|GTC|ACT|ATG|AGC|TGC|AAG|TCC|AGT|CAG|AGT|60|
| |Val|Thr|Met|Ser|Cys|Lys|Ser|Ser|Gln|Ser| |
|61|CTA|TTA|AAC|AGT|GGA|AAT|CAA|AAG|AAC|TAC|90|
| |Leu|Leu|Asn|Ser|Gly|Asn|Gln|Lys|Asn|Tyr| |
|91|TTG|GCC|TGG|TAC|CAA|CAG|AAA|CCA|GGG|CAG|120|
| |Leu|Ala|Trp|Tyr|Gln|Gln|Lys|Pro|Gly|Gln| |
|121|CCT|CCT|AAA|CTT|TTG|ATC|TAC|GGG|GCA|TCC|150|
| |Pro|Pro|Lys|Leu|Leu|Ile|Tyr|Gly|Ala|Ser| |
|151|ACT|AGG|GAA|TCT|GGG|GTC|CCT|GAT|CGC|TTC|180|
| |Thr|Arg|Glu|Ser|Gly|Val|Pro|Asp|Arg|Phe| |
|181|ACA|GGC|AGT|GGA|TCT|GGA|ACC|GAT|TTC|ACT|210|
| |Thr|Gly|Ser|Gly|Ser|Gly|Thr|Asp|Phe|Thr| |
|211|CTT|ACC|ATC|AGC|AGT|GTG|CAG|GCT|GAA|GAC|240|
| |Leu|Thr|Ile|Ser|Ser|Val|Gln|Ala|Glu|Asp| |
|241|CTG|GCA|GTT|TAT|TAC|TGT|CAG|AAT|GAT|CAT|270|
| |Leu|Ala|Val|Tyr|Tyr|Cys|Gln|Asn|Asp|His| |
|271|AGT|TTT|CCA|TTC|ACG|TTC|GGC|TCG|GGG|ACA|300|
| |Ser|Phe|Pro|Phe|Thr|Phe|Gly|Ser|Gly|Thr| |
|301|GAG|TTG|GAA|ATA|AAA| | | | | |315|
| |Glu|Leu|Glu|Ile|Lys| | | | | | |

FIG. 4

```
1    CCT GGC CTG GTG GCG CCC TCA CAG AGC CTG    30
     Pro Gly Leu Val Ala Pro Ser Gln Ser Leu

31   TCC ATC ACT TGC ACT GTC TCT GGG TTT TCA    60
     Ser Ile Thr Cys Thr Val Ser Gly Phe Ser

61   TTA ACC AGC TAT AGT GTA CAC TGG GTT CGC    90
     Leu Thr Ser Tyr Ser Val His Trp Val Arg

91   CAG CCT CCA GGA AAG GGT CTG GAG TGG CTG    120
     Gln Pro Pro Gly Lys Gly Leu Glu Trp Leu

121  GGA GTA ATC TGG GCT AGT GGA GGC ACA GAT    150
     Gly Val Ile Trp Ala Ser Gly Gly Thr Asp

151  TAT AAT TCG GCT CTC ATG TCC AGA CTG AGC    180
     Tyr Asn Ser Ala Leu Met Ser Arg Leu Ser

181  ATC AGC AAA GAC AAC TCC AAG AGC CAA GTT    210
     Ile Ser Lys Asp Asn Ser Lys Ser Gln Val

211  TTC TTA AAA CTG AAC AGT CTG CAA ACT GAT    240
     Phe Leu Lys Leu Asn Ser Leu Gln Thr Asp

241  GAC GCA GCC ATG TAC TAC TGT GCC AGA GAT    270
     Asp Ala Ala Met Tyr Tyr Cys Ala Arg Asp

271  CCC CCT TTT TCC TTA CTA CGG CTT GAC TTC    300
     Pro Pro Phe Ser Leu Leu Arg Leu Asp Phe

301  TGG GGC CAA GGC ACC ACT CTC ACA GTC TCC    330
     Trp Gly Gln Gly Thr Thr Leu Thr Val Ser

331  TCA    333
     Ser
```

FIG. 5

| | | | | | | | | | | | |
|---|---|---|---|---|---|---|---|---|---|---|---|
| 1 | TCC | TCT | CTG | AGT | GTG | TCA | GCA | GGA | GAG | AAG | 30 |
| | Ser | Ser | Leu | Ser | Val | Ser | Ala | Gly | Glu | Lys | |
| 31 | GTC | ACT | ATG | AGC | TGC | AAG | TCC | AGT | CAG | AGT | 60 |
| | Val | Thr | Met | Ser | Cys | Lys | Ser | Ser | Gln | Ser | |
| 61 | CTG | TTA | AAC | AGT | GGA | AAT | CAA | AAA | AAC | TAC | 90 |
| | Leu | Leu | Asn | Ser | Gly | Asn | Gln | Lys | Asn | Tyr | |
| 91 | TTG | GCC | TGG | TAC | CAG | CAG | AAA | CCA | GGG | CAG | 120 |
| | Leu | Ala | Trp | Tyr | Gln | Gln | Lys | Pro | Gly | Gln | |
| 121 | CCT | CCT | AAA | CTT | TTG | ATC | TAC | GGG | GCA | TCC | 150 |
| | Pro | Pro | Lys | Leu | Leu | Ile | Tyr | Gly | Ala | Ser | |
| 151 | ACT | AGG | GAA | TCT | GGG | GTC | CCT | GAT | CGC | TTC | 180 |
| | Thr | Arg | Glu | Ser | Gly | Val | Pro | Asp | Arg | Phe | |
| 181 | ACA | GGC | AGT | GGA | TCT | GGA | ACC | GAT | TTC | ACT | 210 |
| | Thr | Gly | Ser | Gly | Ser | Gly | Thr | Asp | Phe | Thr | |
| 211 | CTT | ACC | ATC | AGC | AGT | GTG | CAG | GCT | GAA | GAC | 240 |
| | Leu | Thr | Ile | Ser | Ser | Val | Gln | Ala | Glu | Asp | |
| 241 | CTG | GCA | GTT | TAT | TAC | TGT | CAG | AAT | GAT | CAT | 270 |
| | Leu | Ala | Val | Tyr | Tyr | Cys | Gln | Asn | Asp | His | |
| 271 | AGT | TTT | CCA | TTC | ACG | TTC | GGC | TCG | GGG | ACA | 300 |
| | Ser | Phe | Pro | Phe | Thr | Phe | Gly | Ser | Gly | Thr | |
| 301 | GAG | TTG | GAA | ATA | AAA | | | | | | 315 |
| | Glu | Leu | Glu | Ile | Lys | | | | | | |

FIG. 6

2B6 CDRs

HEAVY CHAIN 1:   SYSVH
HEAVY CHAIN 2:   VIWASGGTDYNSALMS
HEAVY CHAIN 3:   DPPSSLLRLDY

LIGHT CHAIN 1:   KSSQSLLNSGNQKNYLA
LIGHT CHAIN 2:   GASTRES
LIGHT CHAIN 3:   QNVHSFPFT

2F2 CDRs

HEAVY CHAIN 1:   SYSVH
HEAVY CHAIN 2:   VIWASGGTDYNSALMS
HEAVY CHAIN 3:   DPPSSLLRLDY

LIGHT CHAIN 1:   KSSQSLLNSGNQKNYLA
LIGHT CHAIN 2:   GASTRES
LIGHT CHAIN 3:   QNDHSFPFT

2E3 CDRs

HEAVY CHAIN 1:   SYSVH
HEAVY CHAIN 2:   VIWASGGTDYNSALMS
HEAVY CHAIN 3:   DPPFSLLRLDF

LIGHT CHAIN 1:   KSSQSLLNSGNQKNYLA
LIGHT CHAIN 2:   GASTRES
LIGHT CHAIN 3:   QNDHSFPFT

FIG. 7

| | | | | | | | | | | | |
|---|---|---|---|---|---|---|---|---|---|---|---|
| 1 | CAG | GTT | ACC | CTG | CGT | GAA | TCC | GGT | CCG | GCA | 30 |
| | Gln | Val | Thr | Leu | Arg | Glu | Ser | Gly | Pro | Ala | |
| 31 | CTA | GTT | AAA | CCG | ACC | CAG | ACC | CTG | ACG | TTA | 60 |
| | Leu | Val | Lys | Pro | Thr | Gln | Thr | Leu | Thr | Leu | |
| 61 | ACC | TGC | ACC | GTC | TCC | GGT | TTC | TCC | CTG | ACG | 90 |
| | Thr | Cys | Thr | Val | Ser | Gly | Phe | Ser | Leu | Thr | |
| 91 | AGC | TAT | AGT | GTA | CAC | TGG | GTC | CGT | CAG | CCG | 120 |
| | Ser | Tyr | Ser | Val | His | Trp | Val | Arg | Gln | Pro | |
| 121 | CCG | GGT | AAA | GGT | CTA | GAA | TGG | CTG | GGT | GTA | 150 |
| | Pro | Gly | Lys | Gly | Leu | Glu | Trp | Leu | Gly | Val | |
| 151 | ATA | TGG | GCT | AGT | GGA | GGC | ACA | GAT | TAT | AAT | 180 |
| | Ile | Trp | Ala | Ser | Gly | Gly | Thr | Asp | Tyr | Asn | |
| 181 | TCG | GCT | CTC | ATG | TCC | CGT | CTG | TCG | ATA | TCC | 210 |
| | Ser | Ala | Leu | Met | Ser | Arg | Leu | Ser | Ile | Ser | |
| 211 | AAA | GAC | ACC | TCC | CGT | AAC | CAG | GTT | GTT | CTG | 240 |
| | Lys | Asp | Thr | Ser | Arg | Asn | Gln | Val | Val | Leu | |
| 241 | ACC | ATG | ACT | AAC | ATG | GAC | CCG | GTT | GAC | ACC | 270 |
| | Thr | Met | Thr | Asn | Met | Asp | Pro | Val | Asp | Thr | |
| 271 | GCT | ACC | TAC | TAC | TGC | GCT | CGA | GAT | CCC | CCT | 300 |
| | Ala | Thr | Tyr | Tyr | Cys | Ala | Arg | Asp | Pro | Pro | |
| 301 | TCT | TCC | TTA | CTA | CGG | CTT | GAC | TAC | TGG | GGT | 330 |
| | Ser | Ser | Leu | Leu | Arg | Leu | Asp | Tyr | Trp | Gly | |
| 331 | CGT | GGT | ACC | CCA | GTT | ACC | GTG | AGC | TCA | | 357 |
| | Arg | Gly | Thr | Pro | Val | Thr | Val | Ser | Ser | | |

FIG. 8

| | | | | | | | | | | |
|---|---|---|---|---|---|---|---|---|---|---|
|1|GAT|ATC|GTG|ATG|ACC|CAG|TCT|CCA|GAC|TCG|30
| |Asp|Ile|Val|Met|Thr|Gln|Ser|Pro|Asp|Ser| |
|31|CTA|GCT|GTG|TCT|CTG|GGC|GAG|AGG|GCC|ACC|60
| |Leu|Ala|Val|Ser|Leu|Gly|Glu|Arg|Ala|Thr| |
|61|ATC|AAC|TGC|AAG|AGC|TCT|CAG|AGT|CTG|TTA|90
| |Ile|Asn|Cys|Lys|Ser|Ser|Gln|Ser|Leu|Leu| |
|91|AAC|AGT|GGA|AAT|CAA|AAG|AAC|TAC|TTG|GCC|120
| |Asn|Ser|Gly|Asn|Gln|Lys|Asn|Tyr|Leu|Ala| |
|121|TGG|TAT|CAG|CAG|AAA|CCC|GGG|CAG|CCT|CCT|150
| |Trp|Tyr|Gln|Gln|Lys|Pro|Gly|Gln|Pro|Pro| |
|151|AAG|TTG|CTC|ATT|TAC|GGG|GCG|TCG|ACT|AGG|180
| |Lys|Leu|Leu|Ile|Tyr|Gly|Ala|Ser|Thr|Arg| |
|181|GAA|TCT|GGG|GTA|CCT|GAC|CGA|TTC|AGT|GGC|210
| |Glu|Ser|Gly|Val|Pro|Asp|Arg|Phe|Ser|Gly| |
|211|AGC|GGG|TCT|GGG|ACA|GAT|TTC|ACT|CTC|ACC|240
| |Ser|Gly|Ser|Gly|Thr|Asp|Phe|Thr|Leu|Thr| |
|241|ATC|AGC|AGC|CTG|CAG|GCT|GAA|GAT|GTG|GCA|270
| |Ile|Ser|Ser|Leu|Gln|Ala|Glu|Asp|Val|Ala| |
|271|GTA|TAC|TAC|TGT|CAG|AAT|GTT|CAT|AGT|TTT|300
| |Val|Tyr|Tyr|Cys|Gln|Asn|Val|His|Ser|Phe| |
|301|CCA|TTC|ACG|TTC|GGC|GGA|GGG|ACC|AAG|TTG|330
| |Pro|Phe|Thr|Phe|Gly|Gly|Gly|Thr|Lys|Leu| |
|331|GAG|ATC|AAA| | | | | | | |339
| |Glu|Ile|Lys| | | | | | | | |

FIG. 9

| | | | | | | | | | | |
|---|---|---|---|---|---|---|---|---|---|---|
| 1 | CAG | GTC | CAA | CTG | CAG | GAG | AGC | GGT | CCA | GGT | 30 |
| | Gln | Val | Gln | Leu | Gln | Glu | Ser | Gly | Pro | Gly | |
| 31 | CTT | GTG | AGA | CCT | AGC | CAG | ACC | CTG | AGC | CTG | 60 |
| | Leu | Val | Arg | Pro | Ser | Gln | Thr | Leu | Ser | Leu | |
| 61 | ACC | TGC | ACC | GTC | TCG | GGC | TTC | TCC | CTC | ACC | 90 |
| | Thr | Cys | Thr | Val | Ser | Gly | Phe | Ser | Leu | Thr | |
| 91 | AGC | TAT | AGT | GTA | CAC | TGG | GTG | AGA | CAG | CCA | 120 |
| | Ser | Tyr | Ser | Val | His | Trp | Val | Arg | Gln | Pro | |
| 121 | CCT | GGA | CGA | GGT | CTA | GAG | TGG | CTT | GGA | GTA | 150 |
| | Pro | Gly | Arg | Gly | Leu | Glu | Trp | Leu | Gly | Val | |
| 151 | ATA | TGG | GCT | AGT | GGA | GGC | ACA | GAT | TAT | AAT | 180 |
| | Ile | Trp | Ala | Ser | Gly | Gly | Thr | Asp | Tyr | Asn | |
| 181 | TCG | GCT | CTC | ATG | TCC | AGA | CTG | TCA | ATA | CTG | 210 |
| | Ser | Ala | Leu | Met | Ser | Arg | Leu | Ser | Ile | Leu | |
| 211 | AAA | GAC | AAC | AGC | AAG | AAC | CAG | GTC | AGC | CTG | 240 |
| | Lys | Asp | Asn | Ser | Lys | Asn | Gln | Val | Ser | Leu | |
| 241 | AGA | CTC | AGC | AGC | GTG | ACA | GCC | GCC | GAC | ACC | 270 |
| | Arg | Leu | Ser | Ser | Val | Thr | Ala | Ala | Asp | Thr | |
| 271 | GCG | GTC | TAT | TTC | TGT | GCT | CGA | GAT | CCC | CCT | 300 |
| | Ala | Val | Tyr | Phe | Cys | Ala | Arg | Asp | Pro | Pro | |
| 301 | TCT | TCC | TTA | CTA | CGG | CTT | GAC | TAC | TGG | GGA | 330 |
| | Ser | Ser | Leu | Leu | Arg | Leu | Asp | Tyr | Trp | Gly | |
| 331 | CAA | GGT | ACC | ACG | GTC | ACC | GTC | TCG | AGC | | 357 |
| | Gln | Gly | Thr | Thr | Val | Thr | Val | Ser | Ser | | |

FIG. 12

```
  1  GAT ATC GTG ATG ACC CAG AGC CCA AGC AGC    30
     Asp Ile Val Met Thr Gln Ser Pro Ser Ser

31  CTG AGC GCT AGC GTG GGT GAC AGA GTG ACC    60
     Leu Ser Ala Ser Val Gly Asp Arg Val Thr

61  ATC ACC TGT AAG AGC TCT CAG AGT CTG TTA    90
     Ile Thr Cys Lys Ser Ser Gln Ser Leu Leu

91  AAC AGT GGA AAT CAA AAG AAC TAC TTG GCC   120
     Asn Ser Gly Asn Gln Lys Asn Tyr Leu Ala

121  TGG TAT CAG CAG AAA CCC GGT AAG GCT CCA   150
     Trp Tyr Gln Gln Lys Pro Gly Lys Ala Pro

151  AAG CTG CTG ATC TAC GGG GCA TCG ACT AGG   180
     Lys Leu Leu Ile Tyr Gly Ala Ser Thr Arg

181  GAA TCT GGG GTA CCA GAT AGA TTC AGC GGT   210
     Glu Ser Gly Val Pro Asp Arg Phe Ser Gly

211  AGC GGT AGC GGA ACC GAC TTC ACC TTC ACC   240
     Ser Gly Ser Gly Thr Asp Phe Thr Phe Thr

241  ATC AGC AGC CTG CAG CCA GAG GAC ATC GCC   270
     Ile Ser Ser Leu Gln Pro Glu Asp Ile Ala

271  ACC TAC TAC TGC CAG AAT GTT CAT AGT TTT   300
     Thr Tyr Tyr Cys Gln Asn Val His Ser Phe

301  CCA TTC ACG TTC GGA CAA GGG ACC AAG GTG   330
     Pro Phe Thr Phe Gly Gln Gly Thr Lys Val

331  GAG ATC AAA    339
     Glu Ile Lys
```

FIG. 13

SEQUENCE LISTING (1) GENERAL INFORMATION:

(iii) NUMBER OF SEQUENCES: 50

(2) INFORMATION FOR SEQ ID NO:1:

(i) SEQUENCE CHARACTERISTICS:
      (A) LENGTH: 334 base pairs
      (B) TYPE: nucleic acid
      (C) STRANDEDNESS: single
      (D) TOPOLOGY: linear (ii) MOLECULE TYPE: DNA (genomic)

(ix) FEATURE:
      (A) NAME/KEY: misc_feature
      (B) LOCATION: 1..334
      (D) OTHER INFORMATION: /note= "First base corresponds to
          Kabat position 24"

(xi) SEQUENCE DESCRIPTION: SEQ ID NO:1:

```
ACCTGGCCTG GTGGCGCCCT CACAGAGCCT GTCCATCACT TGCACTGTCT CTGGGTTTTC      60

ATTAACCAGC TATAGTGTAC ACTGGGTTCG CCAGCCTCCA GGAAAGGGTC TGGAGTGGCT     120

GGGAGTAATA TGGGCTAGTG GAGGCACAGA TTATAATTCG GCTCTCATGT CCAGACTGAG     180

CATCAGCAAA GACAACTCCA AGAGCCAAGT TTTCTTAAAA CTGAACAGTC TGCAAACTGA     240

TGACACAGCC ATGTACTACT GTGCCAGAGA TCCCCCTTCT TCCTTACTAC GGCTTGACTA     300

CTGGGGCCAA GGCACCACTC TCACAGTCTC CTCA                                 334
```

(2) INFORMATION FOR SEQ ID NO:2:

(i) SEQUENCE CHARACTERISTICS:
      (A) LENGTH: 315 base pairs
      (B) TYPE: nucleic acid
      (C) STRANDEDNESS: single
      (D) TOPOLOGY: linear (ii) MOLECULE TYPE: DNA (genomic)

(ix) FEATURE:
      (A) NAME/KEY: misc_feature
      (B) LOCATION: 1..315
      (D) OTHER INFORMATION: /note= "First base corresponds to
          Kabat position 25"

(xi) SEQUENCE DESCRIPTION: SEQ ID NO:2:

| | |
|---|---|
| TCCTCCCTGA GTGTGTCAGC AGGAGAGAAG GTCACTATGA GCTGCAAGTC CAGTCAGAGT | 60 |
| CTGTTAAACA GTGGAAATCA AAAGAACTAC TTGGCCTGGT ACCAGCAGAA ACCAGGGCAG | 120 |
| CCTCCTAAAC TTTTGATCTA CGGGGCATCC ACTAGGGAAT CTGGGGTCCC TGATCGCTTC | 180 |
| ACAGGCAGTG GATCTGGAAC CGATTTCACT CTTTCCATCA GCAGTGTGCA GGCTGAAGAC | 240 |
| CTGGCAGTTT ATTACTGTCA GAATGTTCAT AGTTTTCCAT TCACGTTCGG CTCGGGGACA | 300 |
| GAGTTGGAAA TAAAA | 315 |

(2) INFORMATION FOR SEQ ID NO:3:

(i) SEQUENCE CHARACTERISTICS:
        (A) LENGTH: 334 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 1..334
        (D) OTHER INFORMATION: /note= "First base corresponds to
            Kabat position 24"

(xi) SEQUENCE DESCRIPTION: SEQ ID NO:3:

| | |
|---|---|
| ACCTGGCCTG GTGGCGCCCT CACAGAGCCT GTCCATCACT TGCACTGTCT CTGGGTTTTC | 60 |
| ATTAACCAGT TATAGTGTAC ACTGGGTTCG CCAGCCTCCA GGAAAGGGTC TGGAGTGGCT | 120 |
| GGGAGTAATA TGGGCTAGTG GAGGCACAGA TTATAATTCG GCTCTCATGT CCAGACTGAG | 180 |
| CATCAGCAAA GACAACTCCA AGAGCCAAGT TTTCTTAAAA CTGAACAGTC TGCGAACTGA | 240 |
| TGACACAGCC ATGTACTACT GTGCCAGAGA TCCCCCTTCT TCCTTACTAC GGCTTGACTA | 300 |
| CTGGGGCCAA GGCACCACTC TCACAGTCTC CTCA | 334 |

(2) INFORMATION FOR SEQ ID NO:4:

(i) SEQUENCE CHARACTERISTICS:
        (A) LENGTH: 315 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 1..315
        (D) OTHER INFORMATION: /note= "First base corresponds to
            Kabat 25"

(xi) SEQUENCE DESCRIPTION: SEQ ID NO:4:

| | |
|---|---|
| TCCTCCCTGA GTGTGTCAGC AGGAGAGAAG GTCACTATGA GCTGCAAGTC CAGTCAGAGT | 60 |
| CTATTAAACA GTGGAAATCA AAAGAACTAC TTGGCCTGGT ACCAACAGAA ACCAGGGCAG | 120 |
| CCTCCTAAAC TTTTGATCTA CGGGGCATCC ACTAGGGAAT CTGGGGTCCC TGATCGCTTC | 180 |
| ACAGGCAGTG GATCTGGAAC CGATTTCACT CTTACCATCA GCAGTGTGCA GGCTGAAGAC | 240 |
| CTGGCAGTTT ATTACTGTCA GAATGATCAT AGTTTTCCAT TCACGTTCGG CTCGGGGACA | 300 |
| GAGTTGGAAA TAAAA | 315 |

(2) INFORMATION FOR SEQ ID NO:5:

(i) SEQUENCE CHARACTERISTICS:
        (A) LENGTH: 334 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 1..334
        (D) OTHER INFORMATION: /note= "First base corresponds to
            Kabat position 24"

(xi) SEQUENCE DESCRIPTION: SEQ ID NO:5:

```
ACCTGGCCTG GTGGCGCCCT CACAGAGCCT GTCCATCACT TGCACTGTCT CTGGGTTTTC      60

ATTAACCAGC TATAGTGTAC ACTGGGTTCG CCAGCCTCCA GGAAAGGGTC TGGAGTGGCT     120

GGGAGTAATC TGGGCTAGTG GAGGCACAGA TTATAATTCG GCTCTCATGT CCAGACTGAG     180

CATCAGCAAA GACAACTCCA AGAGCCAAGT TTTCTTAAAA CTGAACAGTC TGCAAACTGA     240

TGACGCAGCC ATGTACTACT GTGCCAGAGA TCCCCCTTTT TCCTTACTAC GGCTTGACTT     300

CTGGGGCCAA GGCACCACTC TCACAGTCTC CTCA                                334
```

(2) INFORMATION FOR SEQ ID NO:6:

(i) SEQUENCE CHARACTERISTICS:
        (A) LENGTH: 315 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 1..315
        (D) OTHER INFORMATION: /note= "First base corresponds to
            Kabat position 25"

(xi) SEQUENCE DESCRIPTION: SEQ ID NO:6:

```
TCCTCTCTGA GTGTGTCAGC AGGAGAGAAG GTCACTATGA GCTGCAAGTC CAGTCAGAGT      60

CTGTTAAACA GTGGAAATCA AAAAAACTAC TTGGCCTGGT ACCAGCAGAA ACCAGGGCAG     120

CCTCCTAAAC TTTTGATCTA CGGGGCATCC ACTAGGGAAT CTGGGGTCCC TGATCGCTTC     180

ACAGGCAGTG GATCTGGAAC CGATTTCACT CTTACCATCA GCAGTGTGCA GGCTGAAGAC     240

CTGGCAGTTT ATTACTGTCA GAATGATCAT AGTTTTCCAT TCACGTTCGG CTCGGGGACA     300

GAGTTGGAAA TAAAA                                                      315
```

(2) INFORMATION FOR SEQ ID NO:7:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:7:

```
Ser Tyr Ser Val His
1               5
```

(2) INFORMATION FOR SEQ ID NO:8:

```
    (i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:8:

Val Ile Trp Ala Ser Gly Gly Thr Asp Tyr Asn Ser Ala Leu Met Ser
1               5                   10                  15

(2) INFORMATION FOR SEQ ID NO:9:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:9:

Asp Pro Pro Ser Ser Leu Leu Arg Leu Asp Tyr
1               5                   10

(2) INFORMATION FOR SEQ ID NO:10:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:10:

Lys Ser Ser Gln Ser Leu Leu Asn Ser Gly Asn Gln Lys Asn Tyr Leu
1               5                   10                  15

Ala (2) INFORMATION FOR SEQ ID NO:11:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:11:

Gly Ala Ser Thr Arg Glu Ser
1               5

(2) INFORMATION FOR SEQ ID NO:12:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:12:

Gln Asn Val His Ser Phe Pro Phe Thr
1               5
```

(2) INFORMATION FOR SEQ ID NO:13:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:13:

Gln Asn Asp His Ser Phe Pro Phe Thr
1            5

(2) INFORMATION FOR SEQ ID NO:14:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:14:

Asp Pro Pro Phe Ser Leu Leu Arg Leu Asp Phe
1            5                  10

(2) INFORMATION FOR SEQ ID NO:15:

(i) SEQUENCE CHARACTERISTICS:
        (A) LENGTH: 111 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: misc_feature
        (B) LOCATION: 1..111
        (D) OTHER INFORMATION: /note= "First amino acids corresponds
            to Kabat position 9

(xi) SEQUENCE DESCRIPTION: SEQ ID NO:15:

Pro Gly Leu Val Ala Pro Ser Gln Ser Leu Ser Ile Thr Cys Thr Val
1            5                  10                15

Ser Gly Phe Ser Leu Thr Ser Tyr Ser Val His Trp Val Arg Gln Pro
            20                  25                  30

Pro Gly Lys Gly Leu Glu Trp Leu Gly Val Ile Trp Ala Ser Gly Gly
        35                  40                  45

Thr Asp Tyr Asn Ser Ala Leu Met Ser Arg Leu Ser Ile Ser Lys Asp
    50                  55                  60

Asn Ser Lys Ser Gln Val Phe Leu Lys Leu Asn Ser Leu Gln Thr Asp
65                  70                  75                  80

Asp Thr Ala Met Tyr Tyr Cys Ala Arg Asp Pro Pro Ser Ser Leu Leu
            85                  90                  95

Arg Leu Asp Tyr Trp Gly Gln Gly Thr Thr Leu Thr Val Ser Ser
            100                105              110

(2) INFORMATION FOR SEQ ID NO:16:

(i) SEQUENCE CHARACTERISTICS:
        (A) LENGTH: 105 amino acids
        (B) TYPE: amino acid
        (C) STRANDEDNESS: single (D) TOPOLOGY: linear (ii) MOLECULE TYPE: protein (ix) FEATURE:
            (A) NAME/KEY: misc_feature
            (B) LOCATION: 1..105
            (D) OTHER INFORMATION: /note= "First amino acids corresponds
                to Kabat position 9

(xi) SEQUENCE DESCRIPTION: SEQ ID NO:16:

Ser Ser Leu Ser Val Ser Ala Gly Glu Lys Val Thr Met Ser Cys Lys
1               5                   10                  15

Ser Ser Gln Ser Leu Leu Asn Ser Gly Asn Gln Lys Asn Tyr Leu Ala
                20                  25                  30

Trp Tyr Gln Gln Lys Pro Gly Gln Pro Pro Lys Leu Leu Ile Tyr Gly
            35                  40                  45

Ala Ser Thr Arg Glu Ser Gly Val Pro Asp Arg Phe Thr Gly Ser Gly
        50                  55                  60

Ser Gly Thr Asp Phe Thr Leu Ser Ile Ser Ser Val Gln Ala Glu Asp
65                  70                  75                  80

Leu Ala Val Tyr Tyr Cys Gln Asn Val His Ser Phe Pro Phe Thr Phe
                85                  90                  95

Gly Ser Gly Thr Glu Leu Glu Ile Lys
            100                 105

(2) INFORMATION FOR SEQ ID NO:17:

(i) SEQUENCE CHARACTERISTICS:
            (A) LENGTH: 60 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:17:

ATGGTGTTGC AGACCCAGGT CTTCATTTCT CTGTTGCTCT GGATCTCTGG TGCCTACGGG         60

(2) INFORMATION FOR SEQ ID NO:18:

(i) SEQUENCE CHARACTERISTICS:
            (A) LENGTH: 357 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:18:

CAGGTTACCC TGCGTGAATC CGGTCCGGCA CTAGTTAAAC CGACCCAGAC CCTGACGTTA         60

ACCTGCACCG TCTCCGGTTT CTCCCTGACG AGCTATAGTG TACACTGGGT CCGTCAGCCG        120

CCGGGTAAAG GTCTAGAATG GCTGGGTGTA ATATGGGCTA GTGGAGGCAC AGATTATAAT        180

TCGGCTCTCA TGTCCCGTCT GTCGATATCC AAAGACACCT CCCGTAACCA GGTTGTTCTG        240

ACCATGACTA ACATGGACCC GGTTGACACC GCTACCTACT ACTGCGCTCG AGATCCCCCT        300

TCTTCCTTAC TACGGCTTGA CTACTGGGGT CGTGGTACCC CAGTTACCGT GAGCTCA          357

(2) INFORMATION FOR SEQ ID NO:19:

(i) SEQUENCE CHARACTERISTICS:
            (A) LENGTH: 119 amino acids
            (B) TYPE: amino acid

```
        (C) STRANDEDNESS: single
        (D) TOPOLOGY: linear (ii) MOLECULE TYPE: protein (xi) SEQUENCE DESCRIPTION: SEQ ID NO:19:
```

Gln Val Thr Leu Arg Glu Ser Gly Pro Ala Leu Val Lys Pro Thr Gln
1               5                   10                  15

Thr Leu Thr Leu Thr Cys Thr Val Ser Gly Phe Ser Leu Thr Ser Tyr
            20                  25                  30

Ser Val His Trp Val Arg Gln Pro Pro Gly Lys Gly Leu Glu Trp Leu
        35                  40                  45

Gly Val Ile Trp Ala Ser Gly Gly Thr Asp Tyr Asn Ser Ala Leu Met
    50                  55                  60

Ser Arg Leu Ser Ile Ser Lys Asp Thr Ser Arg Asn Gln Val Val Leu
65                  70                  75                  80

Thr Met Thr Asn Met Asp Pro Val Asp Thr Ala Thr Tyr Tyr Cys Ala
                85                  90                  95

Arg Asp Pro Pro Ser Ser Leu Leu Arg Leu Asp Tyr Trp Gly Arg Gly
            100                 105                 110

Thr Pro Val Thr Val Ser Ser
            115

(2) INFORMATION FOR SEQ ID NO:20:

(i) SEQUENCE CHARACTERISTICS:
        (A) LENGTH: 339 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:20:

```
GATATCGTGA TGACCCAGTC TCCAGACTCG CTAGCTGTGT CTCTGGGCGA GAGGGCCACC      60

ATCAACTGCA AGAGCTCTCA GAGTCTGTTA AACAGTGGAA ATCAAAAGAA CTACTTGGCC     120

TGGTATCAGC AGAAACCCGG GCAGCCTCCT AAGTTGCTCA TTTACGGGGC GTCGACTAGG     180

GAATCTGGGG TACCTGACCG ATTCAGTGGC AGCGGGTCTG GGACAGATTT CACTCTCACC     240

ATCAGCAGCC TGCAGGCTGA AGATGTGGCA GTATACTACT GTCAGAATGT TCATAGTTTT     300

CCATTCACGT TCGGCGGAGG GACCAAGTTG GAGATCAAA                            339
```

(2) INFORMATION FOR SEQ ID NO:21:

(i) SEQUENCE CHARACTERISTICS:
        (A) LENGTH: 113 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:21:

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Gly Asn Gln Lys Asn Tyr Leu Ala Trp Tyr Gln Gln Lys Pro Gly Gln
        35                  40                  45

Pro Pro Lys Leu Leu Ile Tyr Gly Ala Ser Thr Arg Glu Ser Gly Val

```
                50                  55                  60
Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Asn
                 85                  90                  95

Val His Ser Phe Pro Phe Thr Phe Gly Gly Gly Thr Lys Leu Glu Ile
                100                 105                 110

Lys
```

(2) INFORMATION FOR SEQ ID NO:22:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:22:

GTACATATGC AAGGCTTACA ACCACAATC                      29

(2) INFORMATION FOR SEQ ID NO:23:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:23:

GGACAGGGCT TACTAGTGGG CCCTCTGGGC TC                  32

(2) INFORMATION FOR SEQ ID NO:24:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:24:

AGGTSMARCT KTCTCGAGTC WGG                            23

(2) INFORMATION FOR SEQ ID NO:25:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:25:

CTAACACTCA TTCCTGTTGA AGCTCTTGAC AATGGG            36

(2) INFORMATION FOR SEQ ID NO:26:

(i) SEQUENCE CHARACTERISTICS:
        (A) LENGTH: 32 base pairs
        (B) TYPE: nucleic acid (C) STRANDEDNESS: single
            (D) TOPOLOGY: linear (ii) MOLECULE TYPE: DNA (genomic)

(xi) SEQUENCE DESCRIPTION: SEQ ID NO:26:

CCAGATGTGA GCTCGTGATG ACCCAGACTC CA                                    32

(2) INFORMATION FOR SEQ ID NO:27:

(i) SEQUENCE CHARACTERISTICS:
            (A) LENGTH: 140 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:27:

AACCTGCACC GTCTCCGGTT TCTCCCTGAC GAGCTATAGT GTACACTGGG TCCGTCAGCC        60

GCCGGGTAAA GGTCTAGAAT GGCTGGGTGT AATATGGGCT AGTGGAGGCA CAGATTATAA       120

TTCGGCTCTC ATGTCCCGTC                                                  140

(2) INFORMATION FOR SEQ ID NO:28:

(i) SEQUENCE CHARACTERISTICS:
            (A) LENGTH: 149 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:28:

ATATCGACAG ACGGGACATG AGAGCCGAAT TATAATCTGT GCCTCCACTA GCCCATATTA        60

CACCCAGCCA TTCTAGACCT TTACCCGGCG GCTGACGGAC CCAGTGTACA CTATAGCTCG       120

TCAGGGAGAA ACCGGAGACG GTGCAGGTT                                        149

(2) INFORMATION FOR SEQ ID NO:29:

(i) SEQUENCE CHARACTERISTICS:
            (A) LENGTH: 139 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:29:

TGTCGATATC CAAAGACACC TCCCGTAACC AGGTTGTTCT GACCATGACT AACATGGACC        60

CGGTTGACAC CGCTACCTAC TACTGCGCTC GAGATCCCCC TTCTTCCTTA CTACGGCTTG       120

ACTACTGGGG TCGTGGTAC                                                   139

(2) INFORMATION FOR SEQ ID NO:30:

(i) SEQUENCE CHARACTERISTICS:
            (A) LENGTH: 126 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:30:

```
CACGACCCCA GTAGTCAAGC CGTAGTAAGG AAGAAGGGGG ATCTCGAGCG CAGTAGTAGG        60

TAGCGGTGTC AACCGGGTCC ATGTTAGTCA TGGTCAGAAC AACCTGGTTA CGGGAGGTGT       120

CTTTGG                                                                  126

(2) INFORMATION FOR SEQ ID NO:31:

(i) SEQUENCE CHARACTERISTICS:
          (A) LENGTH: 117 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:31:

CTCAGAGTCT GTTAAACAGT GGAAATCAAA AGAACTACTT GGCCTGGTAT CAGCAGAAAC        60

CCGGGCAGCC TCCTAAGTTG CTCATTTACG GGGCGTCGAC TAGGGAATCT GGGGTAC         117

(2) INFORMATION FOR SEQ ID NO:32:

(i) SEQUENCE CHARACTERISTICS:
          (A) LENGTH: 117 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:32:

CCCAGATTCC CTAGTCGACG CCCCGTAAAT GAGCAACTTA GGAGGCTGCC CGGGTTTCTG        60

CTGATACCAG GCCAAGTAGT TCTTTTGATT TCCACTGTTT AACAGACTCT GAGAGCT        117

(2) INFORMATION FOR SEQ ID NO:33:

(i) SEQUENCE CHARACTERISTICS:
          (A) LENGTH: 102 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:33:

GCTGAAGATG TGGCAGTATA CTACTGTCAG AATGTTCATA GTTTTCCATT CACGTTCGGC        60

GGAGGGACCA AGTTGGAGAT CAAACGTACT GTGGCGGCGC CA                         102

(2) INFORMATION FOR SEQ ID NO:34:

(i) SEQUENCE CHARACTERISTICS:
          (A) LENGTH: 111 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:34:

AGCTTGGCGC CGCCACAGTA CGTTTGATCT CCAACTTGGT CCCTCCGCCG AACGTGAATG        60

GAAAACTATG AACATTCTGA CAGTAGTATA CTGCCACATC TTCAGCCTGC A              111

(2) INFORMATION FOR SEQ ID NO:35:

(i) SEQUENCE CHARACTERISTICS:
          (A) LENGTH: 82 base pairs
```

```
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:35:

ATGGTGTTGC AGACCCAGGT CTTCATTTCT CTGTTGCTCT GGATCTCTGG TGCCTACGGG      60

CAGGTTCAAC TGAAAGAGTC AG                                              82

(2) INFORMATION FOR SEQ ID NO:36:

(i) SEQUENCE CHARACTERISTICS:
            (A) LENGTH: 89 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:36:

GTCCTGACTC TTTCAGTTGA ACCTGCCCGT AGGCACCAGA GATCCAGAGC AACAGAGAAA      60

TGAAGACCTG GGTCTGCAAC ACCATGTTG                                       89

(2) INFORMATION FOR SEQ ID NO:37:

(i) SEQUENCE CHARACTERISTICS:
            (A) LENGTH: 45 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:37:

CAAGGCACCA CTCTCACAGT CTCCTCAGCT AGTACGAAGG GCCCA                      45

(2) INFORMATION FOR SEQ ID NO:38:

(i) SEQUENCE CHARACTERISTICS:
            (A) LENGTH: 43 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:38:

AGCTTGGGCC CTTCGTACTA GCTGAGGAGA CTGTGAGTGG TGC                        43

(2) INFORMATION FOR SEQ ID NO:39:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:39:

ATCGTGATGA CCCAGTCTCC ATCCTCCC                                         28

(2) INFORMATION FOR SEQ ID NO:40:

(i) SEQUENCE CHARACTERISTICS:
            (A) LENGTH: 31 base pairs
```

(B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:40:

TCAGGGAGGA TGGAGACTGG GTCATCACGA T                                  31

(2) INFORMATION FOR SEQ ID NO:41:

(i) SEQUENCE CHARACTERISTICS:
          (A) LENGTH: 43 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:41:

TCGGGGACA GAGTTGGAAA TAAAACGTAC TGTGGCGGCG CCA                       43

(2) INFORMATION FOR SEQ ID NO:42:

(i) SEQUENCE CHARACTERISTICS:
          (A) LENGTH: 42 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:42:

AGCTTGGCGC CGCCACAGTA CGTTTTATTT CCAACTCTGT CC                       42

(2) INFORMATION FOR SEQ ID NO:43:

(i) SEQUENCE CHARACTERISTICS:
          (A) LENGTH: 26 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:43:

CTAGCCACCA CCACCACCAC CACTAA                                         26

(2) INFORMATION FOR SEQ ID NO:44:

(i) SEQUENCE CHARACTERISTICS:
          (A) LENGTH: 26 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:44:

CTAGTTAGTG GTGGTGGTGG TGGTGG                                         26

(2) INFORMATION FOR SEQ ID NO:45:

(i) SEQUENCE CHARACTERISTICS:
          (A) LENGTH: 113 amino acids
          (B) TYPE: amino acid
          (C) STRANDEDNESS: single
          (D) TOPOLOGY: linear (ii) MOLECULE TYPE: protein (xi) SEQUENCE DESCRIPTION: SEQ ID NO:45:

```
Glu Leu Val Met Thr Gln Ser Pro Ser Ser Leu Ser Val Ser Ala Gly
1               5                   10                  15

Glu Lys Val Thr Met Ser Cys Lys Ser Ser Gln Ser Leu Leu Asn Ser
                20                  25                  30

Gly Asn Gln Lys Asn Tyr Leu Ala Trp Tyr Gln Gln Lys Pro Gly Gln
            35                  40                  45

Pro Pro Lys Leu Leu Ile Tyr Gly Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp His Ser Tyr Pro Phe Thr Phe Gly Ser Gly Thr Lys Leu Glu Ile
            100                 105                 110

Lys
```

(2) INFORMATION FOR SEQ ID NO:46:

(i) SEQUENCE CHARACTERISTICS:
       (A) LENGTH: 113 amino acids
       (B) TYPE: amino acid
       (C) STRANDEDNESS: single
       (D) TOPOLOGY: linear (ii) MOLECULE TYPE: protein (xi) SEQUENCE DESCRIPTION: SEQ ID NO:46:

```
Glu Leu Val Met Thr Gln Ser Pro Ser Ser Leu Ser Val Ser Ala Gly
1               5                   10                  15

Glu Lys Val Thr Met Ser Cys Lys Ser Ser Gln Ser Leu Leu Asn Ser
                20                  25                  30

Gly Asn Gln Lys Asn Tyr Leu Ala Trp Tyr Gln Gln Lys Pro Gly Gln
            35                  40                  45

Pro Pro Lys Leu Leu Ile Tyr Gly Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ser Tyr Pro Phe Thr Phe Gly Ser Gly Thr Lys Leu Glu Ile
            100                 105                 110

Lys
```

(2) INFORMATION FOR SEQ ID NO:47:

(i) SEQUENCE CHARACTERISTICS:
       (A) LENGTH: 9 amino acids
       (B) TYPE: amino acid
       (C) STRANDEDNESS: single
       (D) TOPOLOGY: linear (ii) MOLECULE TYPE: protein (xi) SEQUENCE DESCRIPTION: SEQ ID NO:47:

```
Gln Asn Asp His Ser Tyr Pro Phe Thr
1               5
```

(2) INFORMATION FOR SEQ ID NO:48:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:48:

```
Gln Asn Asp Tyr Ser Tyr Pro Phe Thr
1               5
```

(2) INFORMATION FOR SEQ ID NO:49:

(i) SEQUENCE CHARACTERISTICS:
        (A) LENGTH: 6285 base pairs
        (B) TYPE: nucleic acid
        (C) STRANDEDNESS: double
        (D) TOPOLOGY: circular (ii) MOLECULE TYPE: DNA (genomic)

(xi) SEQUENCE DESCRIPTION: SEQ ID NO:49:

```
GACGTCGCGG CCGCTCTAGG CCTCCAAAAA AGCCTCCTCA CTACTTCTGG AATAGCTCAG      60
AGGCCGAGGC GGCCTCGGCC TCTGCATAAA TAAAAAAAAT TAGTCAGCCA TGCATGGGGC     120
GGAGAATGGG CGGAACTGGG CGGAGTTAGG GGCGGGATGG GCGGAGTTAG GGGCGGGACT     180
ATGGTTGCTG ACTAATTGAG ATGCATGCTT TGCATACTTC TGCCTGCTGG GGAGCCTGGG     240
GACTTTCCAC ACCTGGTTGC TGACTAATTG AGATGCATGC TTTGCATACT TCTGCCTGCT     300
GGGGAGCCTG GGACTTTCC ACACCCTAAC TGACACACAT TCCACAGAAT TAATTCCCGG     360
GGATCGATCC GTCGACGTAC GACTAGTTAT TAATAGTAAT CAATTACGGG GTCATTAGTT     420
CATAGCCCAT ATATGGAGTT CCGCGTTACA TAACTTACGG TAAATGGCCC GCCTGGCTGA     480
CCGCCCAACG ACCCCCGCCC ATTGACGTCA ATAATGACGT ATGTTCCCAT AGTAACGCCA     540
ATAGGGACTT TCCATTGACG TCAATGGGTG GACTATTTAC GGTAAACTGC CCACTTGGCA     600
GTACATCAAG TGTATCATAT GCCAAGTACG CCCCCTATTG ACGTCAATGA CGGTAAATGG     660
CCCGCCTGGC ATTATGCCCA GTACATGACC TTATGGGACT TTCCTACTTG GCAGTACATC     720
TACGTATTAG TCATCGCTAT TACCATGGTG ATGCGGTTTT GGCAGTACAT CAATGGGCGT     780
GGATAGCGGT TTGACTCACG GGGATTTCCA AGTCTCCACC CCATTGACGT CAATGGGAGT     840
TTGTTTTGGC ACCAAAATCA ACGGGACTTT CCAAAATGTC GTAACAACTC CGCCCCATTG     900
ACGCAAATGG GCGGTAGGCG TGTACGGTGG GAGGTCTATA TAAGCAGAGC TGGGTACGTG     960
AACCGTCAGA TCGCCTGGAG ACGCCATCGA ATTCGAGGAC GCCAGCAACA TGGTGTTGCA    1020
GACCCAGGTC TTCATTTCTC TGTTGCTCTG GATCTCTGGT GCCTACGGGC AGGTTACCCT    1080
GCGTGAATCC GGTCCGGCAC TAGTTAAACC GACCCAGACC CTGACGTTAA CCTGCACCGT    1140
CTCCGGTTTC TCCCTGACGA GCTATAGTGT ACACTGGGTC CGTCAGCCGC GGGTAAAGG    1200
TCTAGAATGG CTGGGTGTAA TATGGGCTAG TGGAGGCACA GATTATAATT CGGCTCTCAT    1260
GTCCCGTCTG TCGATATCCA AAGACACCTC CCGTAACCAG GTTGTTCTGA CCATGACTAA    1320
CATGGACCCG GTTGACACCG CTACCTACTA CTGCGCTCGA GATCCCCCTT CTTCCTTACT    1380
ACGGCTTGAC TACTGGGGTC GTGGTACCCC AGTTACCGTG AGCTCAGCTA GTACCAAGGG    1440
CCCATCGGTC TTCCCCCTGG CACCCTCCTC CAAGAGCACC TCTGGGGGCA CAGCGGCCCT    1500
```

```
GGGCTGCCTG GTCAAGGACT ACTTCCCCGA ACCGGTGACG GTGTCGTGGA ACTCAGGCGC    1560

CCTGACCAGC GGCGTGCACA CCTTCCCGGC TGTCCTACAG TCCTCAGGAC TCTACTCCCT    1620

CAGCAGCGTG GTGACCGTGC CCTCCAGCAG CTTGGGCACC CAGACCTACA TCTGCAACGT    1680

GAATCACAAG CCCAGCAACA CCAAGGTGGA CAAGAGAGTT GAGCCCAAAT CTTGTGACAA    1740

AACTCACACA TGCCCACCGT GCCCAGCACC TGAACTCCTG GGGGGACCGT CAGTCTTCCT    1800

CTTCCCCCCA AAACCCAAGG ACACCCTCAT GATCTCCCGG ACCCCTGAGG TCACATGCGT    1860

GGTGGTGGAC GTGAGCCACG AAGACCCTGA GGTCAAGTTC AACTGGTACG TGGACGGCGT    1920

GGAGGTGCAT AATGCCAAGA CAAAGCCGCG GGAGGAGCAG TACAACAGCA CGTACCGTGT    1980

GGTCAGCGTC CTCACCGTCC TGCACCAGGA CTGGCTGAAT GGCAAGGAGT ACAAGTGCAA    2040

GGTCTCCAAC AAAGCCCTCC CAGCCCCCAT CGAGAAAACC ATCTCCAAAG CCAAAGGGCA    2100

GCCCCGAGAA CCACAGGTGT ACACCCTGCC CCCATCCCGG GAGGAGATGA CCAAGAACCA    2160

GGTCAGCCTG ACCTGCCTGG TCAAAGGCTT CTATCCCAGC GACATCGCCG TGGAGTGGGA    2220

GAGCAATGGG CAGCCGGAGA ACAACTACAA GACCACGCCT CCCGTGCTGG ACTCCGACGG    2280

CTCCTTCTTC CTCTATAGCA AGCTCACCGT GGACAAGAGC AGGTGGCAGC AGGGGAACGT    2340

CTTCTCATGC TCCGTGATGC ATGAGGCTCT GCACAACCAC TACACGCAGA AGAGCCTCTC    2400

CCTGTCTCCG GGTAAGTGAG TGTAGTCTAG ATCTACGTAT GATCAGCCTC GACTGTGCCT    2460

TCTAGTTGCC AGCCATCTGT TGTTTGCCCC TCCCCCGTGC CTTCCTTGAC CCTGGAAGGT    2520

GCCACTCCCA CTGTCCTTTC CTAATAAAAT GAGGAAATTG CATCGCATTG TCTGAGTAGG    2580

TGTCATTCTA TTCTGGGGGG TGGGGTGGGG CAGGACAGCA AGGGGGAGGA TTGGGAAGAC    2640

AATAGCAGGC ATGCTGGGGA TGCGGTGGGC TCTATGGAAC CAGCTGGGGC TCGACAGCGC    2700

TGGATCTCCC GATCCCCAGC TTTGCTTCTC AATTTCTTAT TTGCATAATG AGAAAAAAAG    2760

GAAAATTAAT TTTAACACCA ATTCAGTAGT TGATTGAGCA AATGCGTTGC CAAAAAGGAT    2820

GCTTTAGAGA CAGTGTTCTC TGCACAGATA AGGACAAACA TTATTCAGAG GGAGTACCCA    2880

GAGCTGAGAC TCCTAAGCCA GTGAGTGGCA CAGCATTCTA GGGAGAAATA TGCTTGTCAT    2940

CACCGAAGCC TGATTCCGTA GAGCCACACC TTGGTAAGGG CCAATCTGCT CACACAGGAT    3000

AGAGAGGGCA GGAGCCAGGG CAGAGCATAT AAGGTGAGGT AGGATCAGTT GCTCCTCACA    3060

TTTGCTTCTG ACATAGTTGT GTTGGGAGCT TGGATAGCTT GGACAGCTCA GGGCTGCGAT    3120

TTCGCGCCAA ACTTGACGGC AATCCTAGCG TGAAGGCTGG TAGGATTTTA TCCCCGCTGC    3180

CATCATGGTT CGACCATTGA ACTGCATCGT CGCCGTGTCC CAAAATATGG GGATTGGCAA    3240

GAACGGAGAC CTACCCTGGC CTCCGCTCAG GAACGAGTTC AAGTACTTCC AAAGAATGAC    3300

CACAACCTCT TCAGTGGAAG GTAAACAGAA TCTGGTGATT ATGGGTAGGA AAACCTGGTT    3360

CTCCATTCCT GAGAAGAATC GACCTTTAAA GGACAGAATT AATATAGTTC TCAGTAGAGA    3420

ACTCAAAGAA CCACCACGAG GAGCTCATTT TCTTGCCAAA AGTTTGGATG ATGCCTTAAG    3480

ACTTATTGAA CAACCGGAAT TGGCAAGTAA AGTAGACATG GTTGGATAG TCGGAGGCAG    3540

TTCTGTTTAC CAGGAAGCCA TGAATCAACC AGGCCACCTT AGACTCTTTG TGACAAGGAT    3600

CATGCAGGAA TTTGAAAGTG ACACGTTTTT CCCAGAAATT GATTTGGGGA AATATAAACT    3660

TCTCCCAGAA TACCCAGGCG TCCTCTCTGA GGTCCAGGAG GAAAAAGGCA TCAAGTATAA    3720

GTTTGAAGTC TACGAGAAGA AAGACTAACA GGAAGATGCT TTCAAGTTCT CTGCTCCCCT    3780

CCTAAAGCTA TGCATTTTTA TAAGACCATG GGACTTTTGC TGGCTTTAGA TCAGCCTCGA    3840

CTGTGCCTTC TAGTTGCCAG CCATCTGTTG TTTGCCCCTC CCCCGTGCCT TCCTTGACCC    3900
```

-continued

| | | | | | |
|---|---|---|---|---|---|
| TGGAAGGTGC | CACTCCCACT | GTCCTTTCCT | AATAAAATGA | GGAAATTGCA | TCGCATTGTC | 3960 |
| TGAGTAGGTG | TCATTCTATT | CTGGGGGGTG | GGGTGGGGCA | GGACAGCAAG | GGGGAGGATT | 4020 |
| GGGAAGACAA | TAGCAGGCAT | GCTGGGGATG | CGGTGGGCTC | TATGGAACCA | GCTGGGGCTC | 4080 |
| GATCGAGTGT | ATGACTGCGG | CCGCGATCCC | GTCGAGAGCT | TGGCGTAATC | ATGGTCATAG | 4140 |
| CTGTTTCCTG | TGTGAAATTG | TTATCCGCTC | ACAATTCCAC | ACAACATACG | AGCCGGAAGC | 4200 |
| ATAAAGTGTA | AAGCCTGGGG | TGCCTAATGA | GTGAGCTAAC | TCACATTAAT | TGCGTTGCGC | 4260 |
| TCACTGCCCG | CTTTCCAGTC | GGGAAACCTG | TCGTGCCAGC | TGCATTAATG | AATCGGCCAA | 4320 |
| CGCGCGGGGA | GAGGCGGTTT | GCGTATTGGG | CGCTCTTCCG | CTTCCTCGCT | CACTGACTCG | 4380 |
| CTGCGCTCGG | TCGTTCGGCT | GCGGCGAGCG | GTATCAGCTC | ACTCAAAGGC | GGTAATACGG | 4440 |
| TTATCCACAG | AATCAGGGGA | TAACGCAGGA | AAGAACATGT | GAGCAAAAGG | CCAGCAAAAG | 4500 |
| GCCAGGAACC | GTAAAAAGGC | CGCGTTGCTG | GCGTTTTTCC | ATAGGCTCCG | CCCCCCTGAC | 4560 |
| GAGCATCACA | AAAATCGACG | CTCAAGTCAG | AGGTGGCGAA | ACCCGACAGG | ACTATAAAGA | 4620 |
| TACCAGGCGT | TTCCCCCTGG | AAGCTCCCTC | GTGCGCTCTC | CTGTTCCGAC | CCTGCCGCTT | 4680 |
| ACCGGATACC | TGTCCGCCTT | TCTCCCTTCG | GGAAGCGTGG | CGCTTTCTCA | ATGCTCACGC | 4740 |
| TGTAGGTATC | TCAGTTCGGT | GTAGGTCGTT | CGCTCCAAGC | TGGGCTGTGT | GCACGAACCC | 4800 |
| CCCGTTCAGC | CCGACCGCTG | CGCCTTATCC | GGTAACTATC | GTCTTGAGTC | CAACCCGGTA | 4860 |
| AGACACGACT | TATCGCCACT | GGCAGCAGCC | ACTGGTAACA | GGATTAGCAG | AGCGAGGTAT | 4920 |
| GTAGGCGGTG | CTACAGAGTT | CTTGAAGTGG | TGGCCTAACT | ACGGCTACAC | TAGAAGGACA | 4980 |
| GTATTTGGTA | TCTGCGCTCT | GCTGAAGCCA | GTTACCTTCG | GAAAAAGAGT | TGGTAGCTCT | 5040 |
| TGATCCGGCA | AACAAACCAC | CGCTGGTAGC | GGTGGTTTTT | TTGTTTGCAA | GCAGCAGATT | 5100 |
| ACGCGCAGAA | AAAAAGGATC | TCAAGAAGAT | CCTTTGATCT | TTTCTACGGG | GTCTGACGCT | 5160 |
| CAGTGGAACG | AAAACTCACG | TTAAGGGATT | TTGGTCATGA | GATTATCAAA | AAGGATCTTC | 5220 |
| ACCTAGATCC | TTTTAAATTA | AAAATGAAGT | TTTAAATCAA | TCTAAAGTAT | ATATGAGTAA | 5280 |
| ACTTGGTCTG | ACAGTTACCA | ATGCTTAATC | AGTGAGGCAC | CTATCTCAGC | GATCTGTCTA | 5340 |
| TTTCGTTCAT | CCATAGTTGC | CTGACTCCCC | GTCGTGTAGA | TAACTACGAT | ACGGGAGGGC | 5400 |
| TTACCATCTG | GCCCCAGTGC | TGCAATGATA | CCGCGAGACC | CACGCTCACC | GGCTCCAGAT | 5460 |
| TTATCAGCAA | TAAACCAGCC | AGCCGGAAGG | GCCGAGCGCA | GAAGTGGTCC | TGCAACTTTA | 5520 |
| TCCGCCTCCA | TCCAGTCTAT | TAATTGTTGC | CGGGAAGCTA | GAGTAAGTAG | TTCGCCAGTT | 5580 |
| AATAGTTTGC | GCAACGTTGT | TGCCATTGCT | ACAGGCATCG | TGGTGTCACG | CTCGTCGTTT | 5640 |
| GGTATGGCTT | CATTCAGCTC | CGGTTCCCAA | CGATCAAGGC | GAGTTACATG | ATCCCCCATG | 5700 |
| TTGTGCAAAA | AAGCGGTTAG | CTCCTTCGGT | CCTCCGATCG | TTGTCAGAAG | TAAGTTGGCC | 5760 |
| GCAGTGTTAT | CACTCATGGT | TATGGCAGCA | CTGCATAATT | CTCTTACTGT | CATGCCATCC | 5820 |
| GTAAGATGCT | TTTCTGTGAC | TGGTGAGTAC | TCAACCAAGT | CATTCTGAGA | ATAGTGTATG | 5880 |
| CGGCGACCGA | GTTGCTCTTG | CCCGGCGTCA | ATACGGGATA | ATACCGCGCC | ACATAGCAGA | 5940 |
| ACTTTAAAAG | TGCTCATCAT | TGGAAAACGT | TCTTCGGGGC | GAAAACTCTC | AAGGATCTTA | 6000 |
| CCGCTGTTGA | GATCCAGTTC | GATGTAACCC | ACTCGTGCAC | CCAACTGATC | TTCAGCATCT | 6060 |
| TTTACTTTCA | CCAGCGTTTC | TGGGTGAGCA | AAAACAGGAA | GGCAAAATGC | CGCAAAAAAG | 6120 |
| GGAATAAGGG | CGACACGGAA | ATGTTGAATA | CTCATACTCT | TCCTTTTTCA | ATATTATTGA | 6180 |
| AGCATTTATC | AGGGTTATTG | TCTCATGAGC | GGATACATAT | TTGAATGTAT | TTAGAAAAAT | 6240 |

```
AAACAAATAG GGGTTCCGCG CACATTTCCC CGAAAAGTGC CACCT                      6285

(2) INFORMATION FOR SEQ ID NO:50:

(i) SEQUENCE CHARACTERISTICS:
        (A) LENGTH: 5703 base pairs
        (B) TYPE: nucleic acid
        (C) STRANDEDNESS: double
        (D) TOPOLOGY: circular (ii) MOLECULE TYPE: DNA (genomic)

(xi) SEQUENCE DESCRIPTION: SEQ ID NO:50:

GACGTCGCGG CCGCTCTAGG CCTCCAAAAA AGCCTCCTCA CTACTTCTGG AATAGCTCAG         60

AGGCCGAGGC GGCCTCGGCC TCTGCATAAA TAAAAAAAAT TAGTCAGCCA TGCATGGGGC        120

GGAGAATGGG CGGAACTGGG CGGAGTTAGG GGCGGGATGG GCGGAGTTAG GGGCGGGACT        180

ATGGTTGCTG ACTAATTGAG ATGCATGCTT TGCATACTTC TGCCTGCTGG GGAGCCTGGG        240

GACTTTCCAC ACCTGGTTGC TGACTAATTG AGATGCATGC TTTGCATACT TCTGCCTGCT        300

GGGGAGCCTG GGGACTTTCC ACACCCTAAC TGACACACAT TCCACAGAAT TAATTCCCGG        360

GGATCGATCC GTCGACGTAC GACTAGTTAT TAATAGTAAT CAATTACGGG GTCATTAGTT        420

CATAGCCCAT ATATGGAGTT CCGCGTTACA TAACTTACGG TAAATGGCCC GCCTGGCTGA        480

CCGCCCAACG ACCCCCGCCC ATTGACGTCA ATAATGACGT ATGTTCCCAT AGTAACGCCA        540

ATAGGGACTT TCCATTGACG TCAATGGGTG GACTATTTAC GGTAAACTGC CCACTTGGCA        600

GTACATCAAG TGTATCATAT GCCAAGTACG CCCCCTATTG ACGTCAATGA CGGTAAATGG        660

CCCGCCTGGC ATTATGCCCA GTACATGACC TTATGGGACT TTCCTACTTG GCAGTACATC        720

TACGTATTAG TCATCGCTAT TACCATGGTG ATGCGGTTTT GGCAGTACAT CAATGGGCGT        780

GGATAGCGGT TTGACTCACG GGGATTTCCA AGTCTCCACC CCATTGACGT CAATGGGAGT        840

TTGTTTTGGC ACCAAAATCA ACGGGACTTT CCAAAATGTC GTAACAACTC CGCCCCATTG        900

ACGCAAATGG GCGGTAGGCG TGTACGGTGG GAGGTCTATA TAAGCAGAGC TGGGTACGTG        960

AACCGTCAGA TCGCCTGGAG ACGCCATCGA ATTCATTGAT AGGATCCAGC AAGATGGTGT       1020

TGCAGACCCA GGTCTTCATT TCTCTGTTGC TCTGGATCTC TGGTGCCTAC GGGGATATCG       1080

TGATGACCCA GTCTCCAGAC TCGCTAGCTG TGTCTCTGGG CGAGAGGGCC ACCATCAACT       1140

GCAAGAGCTC TCAGAGTCTG TTAAACAGTG GAAATCAAAA GAACTACTTG GCCTGGTATC       1200

AGCAGAAACC CGGGCAGCCT CCTAAGTTGC TCATTTACGG GGCGTCGACT AGGGAATCTG       1260

GGGTACCTGA CCGATTCAGT GGCAGCGGGT CTGGGACAGA TTTCACTCTC ACCATCAGCA       1320

GCCTGCAGGC TGAAGATGTG GCAGTATACT ACTGTCAGAA TGTTCATAGT TTTCCATTCA       1380

CGTTCGGCGG AGGGACCAAG TTGGAGATCA AACGTACTGT GGCGGCGCCA TCTGTCTTCA       1440

TCTTCCCGCC ATCTGATGAG CAGTTGAAAT CTGGAACTGC CTCTGTTGTG TGCCTGCTGA       1500

ATAACTTCTA TCCCAGAGAG GCCAAAGTAC AGTGGAAGGT GGATAACGCC CTCCAATCGG       1560

GTAACTCCCA GGAGAGTGTC ACAGAGCAGG ACAGCAAGGA CAGCACCTAC AGCCTCAGCA       1620

GCACCCTGAC GCTGAGCAAA GCAGACTACG AGAAACACAA AGTCTACGCC TGCGAAGTCA       1680

CCCATCAGGG CCTGAGCTCG CCCGTCACAA AGAGCTTCAA CAGGGGAGAG TGTTAATTCT       1740

AGATCCGTTA TCTACGTATG ATCAGCCTCG ACTGTGCCTT CTAGTTGCCA GCCATCTGTT       1800

GTTTGCCCCT CCCCCGTGCC TTCCTTGACC CTGGAAGGTG CCACTCCCAC TGTCCTTTCC       1860

TAATAAAATG AGGAAATTGC ATCGCATTGT CTGAGTAGGT GTCATTCTAT TCTGGGGGGT       1920
```

-continued

```
GGGGTGGGGC AGGACAGCAA GGGGGAGGAT TGGGAAGACA ATAGCAGGCA TGCTGGGGAT      1980

GCGGTGGGCT CTATGGAACC AGCTGGGGCT CGACAGCTCG AGCTAGCTTT GCTTCTCAAT      2040

TTCTTATTTG CATAATGAGA AAAAAAGGAA AATTAATTTT AACACCAATT CAGTAGTTGA      2100

TTGAGCAAAT GCGTTGCCAA AAAGGATGCT TTAGAGACAG TGTTCTCTGC ACAGATAAGG      2160

ACAAACATTA TTCAGAGGGA GTACCCAGAG CTGAGACTCC TAAGCCAGTG AGTGGCACAG      2220

CATTCTAGGG AGAAATATGC TTGTCATCAC CGAAGCCTGA TTCCGTAGAG CCACACCTTG      2280

GTAAGGGCCA ATCTGCTCAC ACAGGATAGA GAGGGCAGGA GCCAGGGCAG AGCATATAAG      2340

GTGAGGTAGG ATCAGTTGCT CCTCACATTT GCTTCTGACA TAGTTGTGTT GGGAGCTTGG      2400

ATCGATCCAC CATGGTTGAA CAAGATGGAT TGCACGCAGG TTCTCCGGCC GCTTGGGTGG      2460

AGAGGCTATT CGGCTATGAC TGGGCACAAC AGACAATCGG CTGCTCTGAT GCCGCCGTGT      2520

TCCGGCTGTC AGCGCAGGGG CGCCCGGTTC TTTTTGTCAA GACCGACCTG TCCGGTGCCC      2580

TGAATGAACT GCAGGACGAG GCAGCGCGGC TATCGTGGCT GGCCACGACG GGCGTTCCTT      2640

GCGCAGCTGT GCTCGACGTT GTCACTGAAG CGGGAAGGGA CTGGCTGCTA TTGGGCGAAG      2700

TGCCGGGGCA GGATCTCCTG TCATCTCACC TTGCTCCTGC CGAGAAAGTA TCCATCATGG      2760

CTGATGCAAT GCGGCGGCTG CATACGCTTG ATCCGGCTAC CTGCCCATTC GACCACCAAG      2820

CGAAACATCG CATCGAGCGA GCACGTACTC GGATGGAAGC CGGTCTTGTC GATCAGGATG      2880

ATCTGGACGA AGAGCATCAG GGGCTCGCGC CAGCCGAACT GTTCGCCAGG CTCAAGGCGC      2940

GCATGCCCGA CGGCGAGGAT CTCGTCGTGA CCCATGGCGA TGCCTGCTTG CCGAATATCA      3000

TGGTGGAAAA TGGCCGCTTT TCTGGATTCA TCGACTGTGG CCGGCTGGGT GTGGCGGACC      3060

GCTATCAGGA CATAGCGTTG GCTACCCGTG ATATTGCTGA AGAGCTTGGC GGCGAATGGG      3120

CTGACCGCTT CCTCGTGCTT TACGGTATCG CCGCTCCCGA TTCGCAGCGC ATCGCCTTCT      3180

ATCGCCTTCT TGACGAGTTC TTCTGAGCGG GACTCTGGGG TTCGAAATGA CCGACCAAGC      3240

GACGCCCAAC CTGCCATCAC GAGATTTCGA TTCCACCGCC GCCTTCTATG AAAGGTTGGG      3300

CTTCGGAATC GTTTTCCGGG ACGCCGGCTG GATGATCCTC CAGCGCGGGG ATCTCATGCT      3360

GGAGTTCTTC GCCCACCCCA ACTTGTTTAT TGCAGCTTAT AATGGTTACA AATAAAGCAA      3420

TAGCATCACA AATTTCACAA ATAAAGCATT TTTTTCACTG CATTCTAGTT GTGGTTTGTC      3480

CAAACTCATC AATGTATCTT ATCATGTCTG GATCGCGGCC GCGATCCCGT CGAGAGCTTG      3540

GCGTAATCAT GGTCATAGCT GTTTCCTGTG TGAAATTGTT ATCCGCTCAC AATTCCACAC      3600

AACATACGAG CCGGAAGCAT AAAGTGTAAA GCCTGGGGTG CCTAATGAGT GAGCTAACTC      3660

ACATTAATTG CGTTGCGCTC ACTGCCCGCT TTCCAGTCGG GAAACCTGTC GTGCCAGCTG      3720

CATTAATGAA TCGGCCAACG CGCGGGGAGA GGCGGTTTGC GTATTGGGCG CTCTTCCGCT      3780

TCCTCGCTCA CTGACTCGCT GCGCTCGGTC GTTCGGCTGC GGCGAGCGGT ATCAGCTCAC      3840

TCAAAGGCGG TAATACGGTT ATCCACAGAA TCAGGGGATA ACGCAGGAAA GAACATGTGA      3900

GCAAAAGGCC AGCAAAAGGC CAGGAACCGT AAAAAGGCCG CGTTGCTGGC GTTTTTCCAT      3960

AGGCTCCGCC CCCCTGACGA GCATCACAAA AATCGACGCT CAAGTCAGAG GTGGCGAAAC      4020

CCGACAGGAC TATAAAGATA CCAGGCGTTT CCCCCTGGAA GCTCCCTCGT GCGCTCTCCT      4080

GTTCCGACCC TGCCGCTTAC CGGATACCTG TCCGCCTTTC TCCCTTCGGG AAGCGTGGCG      4140

CTTTCTCAAT GCTCACGCTG TAGGTATCTC AGTTCGGTGT AGGTCGTTCG CTCCAAGCTG      4200

GGCTGTGTGC ACGAACCCCC CGTTCAGCCC GACCGCTGCG CCTTATCCGG TAACTATCGT      4260

CTTGAGTCCA ACCCGGTAAG ACACGACTTA TCGCCACTGG CAGCAGCCAC TGGTAACAGG      4320
```

```
                                    -continued
ATTAGCAGAG CGAGGTATGT AGGCGGTGCT ACAGAGTTCT TGAAGTGGTG GCCTAACTAC    4380

GGCTACACTA GAAGGACAGT ATTTGGTATC TGCGCTCTGC TGAAGCCAGT TACCTTCGGA    4440

AAAAGAGTTG GTAGCTCTTG ATCCGGCAAA CAAACCACCG CTGGTAGCGG TGGTTTTTTT    4500

GTTTGCAAGC AGCAGATTAC GCGCAGAAAA AAAGGATCTC AAGAAGATCC TTTGATCTTT    4560

TCTACGGGGT CTGACGCTCA GTGGAACGAA AACTCACGTT AAGGGATTTT GGTCATGAGA    4620

TTATCAAAAA GGATCTTCAC CTAGATCCTT TTAAATTAAA AATGAAGTTT TAAATCAATC    4680

TAAAGTATAT ATGAGTAAAC TTGGTCTGAC AGTTACCAAT GCTTAATCAG TGAGGCACCT    4740

ATCTCAGCGA TCTGTCTATT TCGTTCATCC ATAGTTGCCT GACTCCCCGT CGTGTAGATA    4800

ACTACGATAC GGGAGGGCTT ACCATCTGGC CCCAGTGCTG CAATGATACC GCGAGACCCA    4860

CGCTCACCGG CTCCAGATTT ATCAGCAATA AACCAGCCAG CCGGAAGGGC CGAGCGCAGA    4920

AGTGGTCCTG CAACTTTATC CGCCTCCATC CAGTCTATTA ATTGTTGCCG GGAAGCTAGA    4980

GTAAGTAGTT CGCCAGTTAA TAGTTTGCGC AACGTTGTTG CCATTGCTAC AGGCATCGTG    5040

GTGTCACGCT CGTCGTTTGG TATGGCTTCA TTCAGCTCCG GTTCCCAACG ATCAAGGCGA    5100

GTTACATGAT CCCCCATGTT GTGCAAAAAA GCGGTTAGCT CCTTCGGTCC TCCGATCGTT    5160

GTCAGAAGTA AGTTGGCCGC AGTGTTATCA CTCATGGTTA TGGCAGCACT GCATAATTCT    5220

CTTACTGTCA TGCCATCCGT AAGATGCTTT TCTGTGACTG GTGAGTACTC AACCAAGTCA    5280

TTCTGAGAAT AGTGTATGCG GCGACCGAGT TGCTCTTGCC CGGCGTCAAT ACGGGATAAT    5340

ACCGCGCCAC ATAGCAGAAC TTTAAAAGTG CTCATCATTG GAAAACGTTC TTCGGGGCGA    5400

AAACTCTCAA GGATCTTACC GCTGTTGAGA TCCAGTTCGA TGTAACCCAC TCGTGCACCC    5460

AACTGATCTT CAGCATCTTT TACTTTCACC AGCGTTTCTG GGTGAGCAAA AACAGGAAGG    5520

CAAAATGCCG CAAAAAAGGG AATAAGGGCG ACACGGAAAT GTTGAATACT CATACTCTTC    5580

CTTTTTCAAT ATTATTGAAG CATTTATCAG GGTTATTGTC TCATGAGCGG ATACATATTT    5640

GAATGTATTT AGAAAAATAA ACAAATAGGG GTTCCGCGCA CATTTCCCCG AAAAGTGCCA    5700

CCT                                                                 5703
```

RECOMBINANT IL-5 ANTAGONISTS USEFUL IN TREATMENT OF IL-5 MEDIATED DISORDERS

CROSS REFERENCE TO RELATED APPLICATIONS

This is a national stage filing under 35 U.S.C. §371 of PCT/US95/17082 filed Dec. 22, 1995, which is a continuation-in-part of application Ser. Nos. 08/470,110, now U.S. Pat. No. 5,693,323, and Ser. No. 08/467,420, now U.S. Pat. No. 5,683,892, both filed Jun. 6, 1995, which are continuations-in-part of application Ser. No. 08/363,131 filed Dec. 23, 1994, now abandoned.

FIELD OF THE INVENTION

The present invention relates generally to the field of antibodies and altered antibodies, useful in the treatment and diagnosis of conditions mediated by IL-5 and excess eosinophil production, and more specifically to mAbs, Fabs, chimeric and humanized antibodies.

BACKGROUND OF THE INVENTION

Eosinophils have been implicated in the pathogenesis of a wide variety of inflammatory disease states including allergic disorders associated with hypersensitivity reactions in the lung tissue (Butterfield et al., In: *Immunopharmacology of Eosinophils*, H. Smith and R. Cook, Eds., p. 151–192, Academic Press, London (1993)). A notable example is asthma, a disease characterized by reversible obstruction of the airways leading to non-specific bronchial hyperresponsiveness. This in turn is dependent upon the generation of a chronic inflammatory reaction at the level of the bronchial mucosa and a characteristic infiltration by macrophages, lymphocytes and eosinophils. The eosinophil appears to play a central role in initiating the mucosal damage typical of the disease (Corrigan et al., *Immunol. Today*, 13:501–507 (1992)). Increased numbers of activated eosinophils have been reported in the circulation, bronchial secretions and lung parenchyma of patients with chronic asthma, and the severity of the disease, as measured by a variety of lung function tests, correlates with blood eosinophil numbers (Griffen et al., *J. Aller. Clin. Immunol.*, 67:548–557 (1991)). Increased numbers of eosinophils, often in the process of degranulation, have also been recovered in bronchoalveolar lavage (BAL) fluids of patients undergoing late asthmatic reactions, and reducing eosinophil numbers, usually as a consequence of steroid therapy, is associated with improvements in clinical symptoms (Bousquet et al., *N. Eng. J. Med.*, 323:1033–1039 (1990)).

Interleukin 5 (IL-5) is a homodimeric glycoprotein produced predominantly by activated CD4+T lymphocytes. In man, IL-5 is largely responsible for controlling the growth and differentiation of eosinophils. Elevated levels of IL-5 are detected in the bronchoalveolar lavage washings of asthmatics (Motojima et al., *Allergy*, 48:98 (1993)). Mice which are transgenic for IL-5 show a marked eosinophilia in peripheral blood and tissues in the absence of antigenic stimulation (Dent et al., *J. Exp. Med.*, 172:1425 (1990)) and anti-murine IL-5 monoclonal antibodies have been shown to have an effect in reducing eosinophilia in the blood and tissues of mice (Hitoshi et al., *Int. Immunol.*, 3:135 (1991)) as well as the eosinophilia associated with parasite infection and allergen challenge in experimental animals (Coffman et al., *Science*, 245:308–310 (1989), Sher et al., *Proc. Natl. Acad. Sci.*, 83:61–65 (1990), Chand et al., *Eur. J. Pharmacol.*, 211:121–123 (1992)).

Although corticosteroids are extremely effective in suppressing eosinophil numbers and other inflammatory components of asthma, there are concerns about their side effects in both severe asthmatics and more recently in mild to moderate asthmatics. The only other major anti-inflammatory drug therapies—cromoglycates (cromolyn sodium and nedocromil)—are considerably less effective than corticosteroids and their precise mechanism of action remains unknown.

More recent developments have focused on new inhaled steroids, longer acting bronchodilators and agents acting on novel biochemical or pharmacological targets (e.g., potassium channel activators, leukotriene antagonists, 5-lipoxygenase (5-LO) inhibitors etc.). An ideal drug would be one that combines the efficacy of steroids with the safety associated with cromolyn sodium, yet has increased selectivity and more rapid onset of action. Neutralizing IL-5 antibodies may potentially be useful in relieving eosinophila-related symptoms in man.

Hence there is a need in the art for a high affinity IL-5 antagonist, such as a neutralizing monoclonal antibody to human interleukin 5, which would reduce eosinophil differentiation and proliferation (i.e., accumulation of eosinophils) and thus eosinophil inflammation.

SUMMARY OF THE INVENTION

In a first aspect, the present invention provides rodent (e.g., rat and murine) neutralizing monoclonal antibodies specific for human interleukin-5 and having a binding affinity characterized by a dissociation constant equal to or less than about $3.5 \times 10^{-11}$ M as described in the detailed description. Exemplary of such monoclonal antibodies are the murine monoclonal antibodies 2B6, 2E6 and 2F2 and rat monoclonal antibodies such as 4A6. Another aspect of the invention are hybridomas such as SK119-2B6.206.75(1), SK119-2E3.39.40.2, SK119-2F2.37.80.12, 4A6(1)G1F7 and 5D3(1)F5D6.

In a related aspect, the present invention provides neutralizing Fab fragments or F(ab')$_2$ fragments thereof specific for human interleukin-5 produced by deleting the Fc region of the rodent neutralizing monoclonal antibodies of the present invention.

In yet another related aspect, the present invention provides neutralizing Fab fragments or F(ab')$_2$ fragments thereof specific for human interleukin-5 produced by the chain shuffling technique whereby a heavy (or light) chain immnunoglobulin, isolated from rodent neutralizing monoclonal antibodies of the invention, is expressed with a light chain (or heavy chain, respectively) immunoglobulin library isolated from interleukin-5 immunized rodents, in a filamentous phage Fab display library.

In still another related aspect, the present invention provides an altered antibody specific for human interleukin-5 which comprises complementarity determining regions (CDRs) derived from a non-human neutralizing monoclonal antibody (mAb) characterized by a dissociation constant equal to or less than about $3.5 \times 10^{-11}$ M for human interleukin-5 and nucleic acid molecules encoding the same. When the altered antibody is a humanized antibody, the sequences that encode complementarity determining regions (CDRs) from a non-human immunoglobulin are inserted into a first immunoglobulin partner in which at least one, and preferably all complementarity determining regions (CDRs) of the first immunoglobulin partner are replaced by CDRs from the non-human monoclonal antibody. Preferably, the first immunoglobulin partner is operatively linked to a second immunoglobulin partner as well, which comprises all or a part of an immunoglobulin constant chain.

In a related aspect, the present invention provides CDRs derived from non-human neutralizing monoclonal antibodies (mAbs) characterized by a dissociation constant equal to or less than about $3.5 \times 10^{-11}$ M for human interleukin-5, and nucleic acid molecules encoding such CDRs.

In still another aspect, there is provided a chimeric antibody containing human heavy and light chain constant regions and heavy and light chain variable regions derived from non-human neutralizing monoclonal antibodies characterized by a dissociation constant equal to or less than about $3.5 \times 10^{-11}$ M for human interleukin-5.

In yet another aspect, the present invention provides a pharmaceutical composition which contains one (or more) of the above-described altered antibodies and a pharmaceutically acceptable carrier.

In a further aspect, the present invention provides a method for treating conditions in humans associated with excess eosinophil production by administering to said human an effective amount of the pharmaceutical composition of the invention.

In yet another aspect, the present invention provides methods for, and components useful in, the recombinant production of altered antibodies (e.g., engineered antibodies, CDRs, Fab or F(ab)$_2$ fragments, or analogs thereof) which are derived from non-human neutralizing monoclonal antibodies (mAbs) characterized by a dissociation constant equal to or less than $3.5 \times 10^{-11}$ M for human IL-5. These components include isolated nucleic acid sequences encoding same, recombinant plasmids containing the nucleic acid sequences under the control of selected regulatory sequences which are capable of directing the expression thereof in host cells (preferably mammalian) transfected with the recombinant plasmids. The production method involves culturing a transfected host cell line of the present invention under conditions such that an altered antibody, preferably a humanized antibody, is expressed in said cells and isolating the expressed product therefrom.

In yet another aspect of the invention is a method to diagnose conditions associated with excess eosinophil production in a human which comprises obtaining a sample of biological fluid from a patient and allowing the antibodies and altered antibodies of the instant invention to come in contact with such sample under conditions such that an IL-5/(monoclonal or altered) antibody complex is formed and detecting the presence or absence of said IL-5/antibody complex.

Other aspects and advantages of the present invention are described further in the detailed description and the preferred embodiments thereof.

BRIEF DESCRIPTION OF THE DRAWINGS

FIG. 1 [SEQ ID NOs: 1 and 15] illustrates the heavy chain variable region for the murine antibody 2B6, and the murine/human 2B6 chimeric antibody. The boxed areas indicate the CDRs.

FIG. 2 [SEQ ID NOs: 2 and 16] illustrates the light chain variable region for the murine antibody 2B6, and the murine/human 2B6 chimeric antibody. The boxed areas indicate the CDRs.

FIG. 3 [SEQ ID NO:3] illustrates the heavy chain variable region for the murine antibody 2F2. The boxed areas indicate the CDRs.

FIG. 4 [SEQ ID NO:4] illustrates the light chain variable region for the murine antibody 2F2. The boxed areas indicate the CDRs.

FIG. 5 [SEQ ID NO:5] illustrates the heavy chain variable region for the murine antibody 2E3. The boxed areas indicate the CDRs.

FIG. 6 [SEQ ID NO:6] illustrates the light chain variable region for the murine antibody 2E3. The boxed areas indicate the CDRs.

FIG. 7 [SEQ ID NOs:7–14] illustrates the heavy and light chain CDRs from murine antibodies 2B6, 2F2 and 2E3.

FIG. 8 [SEQ ID NOs: 18, 19] illustrates the heavy chain variable region for the humanized antibody 2B6. The boxed areas indicate the CDRs.

FIG. 9 [SEQ ID NOs: 20, 21] illustrates the light chain variable region for the humanized antibody 2B6. The boxed areas indicate the CDRs.

FIG. 12 [SEQ ID NOs: 61, 62] illustrates the NewM heavy chain variable region for the humanized antibody 2B6. The boxed areas indicate the CDRs.

FIG. 13 [SEQ ID NOs: 69, 70] illustrates the REI light chain variable region for the humanized antibody 2B6. The boxed areas indicate the CDRs.

DETAILED DESCRIPTION OF THE INVENTION

Figure 10:
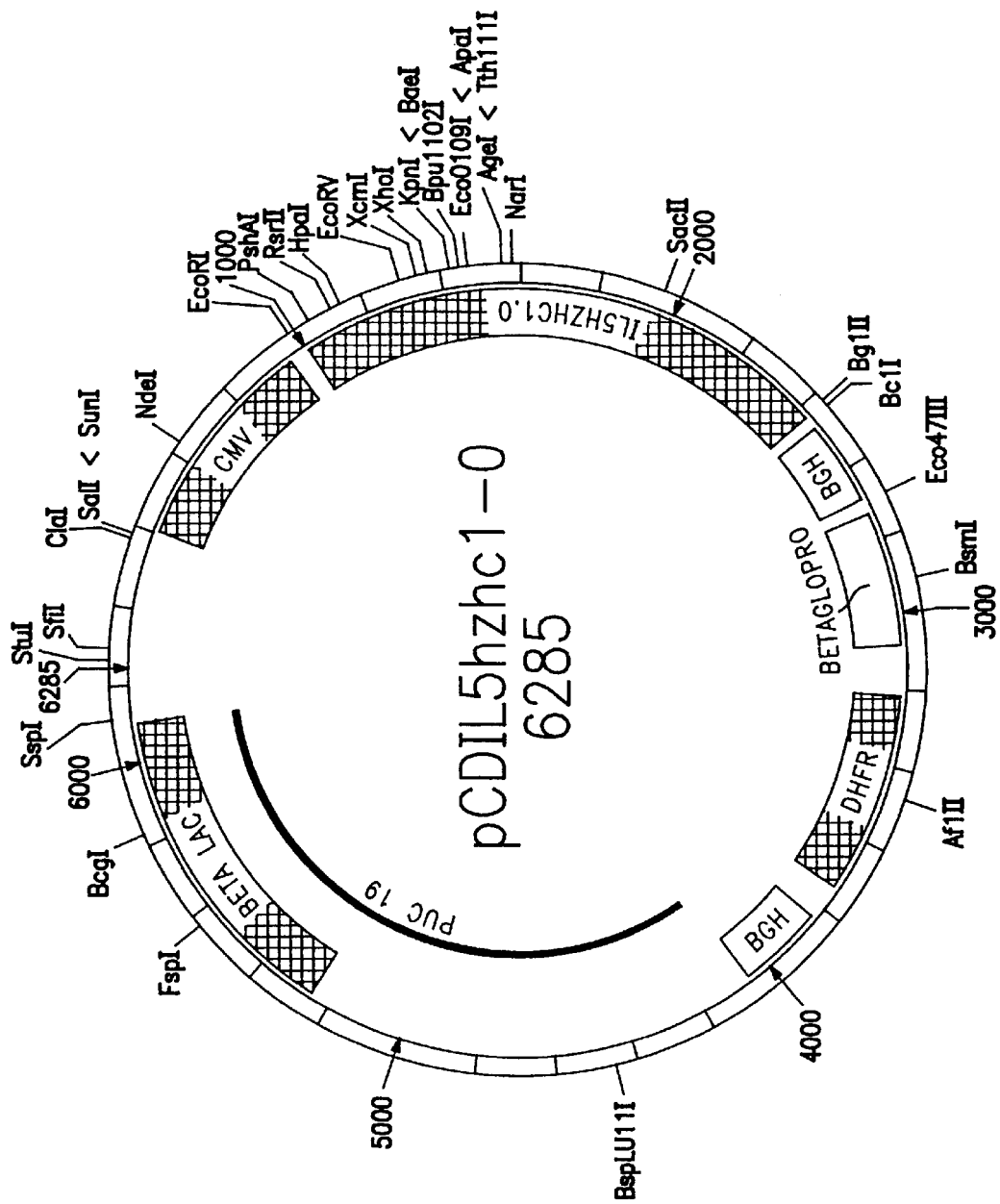
FIG. 10 is a schematic drawing of plasmid pCDIL5HZHC1.0 employed to express a humanized heavy chain gene in mammalian cells. The plasmid contains a beta lactamase gene (BETA LAC), an SV-40 origin of replication (SV40), a cytomegalovirus promoter sequence (CMV), a signal sequence, the humanized heavy chain, a poly A signal from bovine growth hormone (BGH), a betaglobin promoter (beta glopro), a dihydrofolate reductase gene (DHFR), and another BGH sequence poly A signal in a pUC19 background.

The present invention provides a variety of antibodies, altered antibodies and fragments thereof, which are characterized by human IL-5 binding specificity, neutralizing activity, and high affinity for human IL-5 as exemplified in murine monoclonal antibody 2B6. The antibodies of the present invention were prepared by conventional hybridoma techniques, phage display combinatorial libraries, immunoglobulin chain shuffling, and humanization techniques to generate novel neutralizing antibodies. These products are useful in therapeutic and pharmaceutical compositions for treating IL-5-mediated disorders, e.g., asthma. These products are also useful in the diagnosis of IL-5-mediated conditions by measurement (e.g., enzyme linked immunosorbent assay (ELISA)) of endogenous IL-5 levels in humans or IL-5 released ex vivo from activated cells.

I. Definitions.

"Altered antibody" refers to a protein encoded by an altered immunoglobulin coding region, which may be obtained by expression in a selected host cell. Such altered antibodies are engineered antibodies (e.g., chimeric or humanized antibodies) or antibody fragments lacking all or part of an immunoglobulin constant region, e.g., Fv, Fab, or F(ab)$_2$ and the like.

"Altered immunoglobulin coding region" refers to a nucleic acid sequence encoding altered antibody of the invention. When the altered antibody is a CDR-grafted or humanized antibody, the sequences that encode the complementarity determining regions (CDRs) from a non-human immunoglobulin are inserted into a first immunoglobulin partner comprising human variable framework sequences. Optionally, the first immunoglobulin partner is operatively linked to a second immunoglobulin partner.

"First immunoglobulin partner" refers to a nucleic acid sequence encoding a human framework or human immunoglobulin variable region in which the native (or naturally-occurring) CDR-encoding regions are replaced by the CDR-encoding regions of a donor antibody. The human variable region can be an immunoglobulin heavy chain, a light chain (or both chains), an analog or functional fragments thereof. Such CDR regions, located within the variable region of antibodies (immunoglobulins) can be determined by known methods in the art. For example Kabat et al. (*Sequences of Proteins of Immunological Interest*, 4th Ed., U.S. Department of Health and Human Services, National Institutes of Health (1987)) disclose rules for locating CDRs. In addition, computer programs are known which are useful for identifying CDR regions/structures.

"Neutralizing" refers to an antibody that inhibits IL-5 activity by preventing the binding of human IL-5 to its specific receptor or by inhibiting the signaling of IL-5 through its receptor, should binding occur. A mAb is neutralizing if it is 90% effective, preferably 95% effective and most preferably 100% effective in inhibiting IL-5 activity as measured in the B13 cell bioassay (IL-5 Neutralization assay, see Example 2C).

The term "high affinity" refers to an antibody having a binding affinity characterized by a $K_d$ equal to or less than $3.5 \times 10^{-11}$ M for human IL-5 as determined by optical biosensor analysis (see Example 2D).

By "binding specificity for human IL-5" is meant a high affinity for human, not murine, IL-5.

"Second immunoglobulin partner" refers to another nucleotide sequence encoding a protein or peptide to which the first immunoglobulin partner is fused in frame or by means of an optional conventional linker sequence (i.e., operatively linked). Preferably it is an immunoglobulin gene. The second immunoglobulin partner may include a nucleic acid sequence encoding the entire constant region for the same (i.e., homologous—the first and second altered antibodies are derived from the same source) or an additional (i.e., heterologous) antibody of interest. It may be an immunoglobulin heavy chain or light chain (or both chains as part of a single polypeptide). The second immunoglobulin partner is not limited to a particular immunoglobulin class or isotype. In addition, the second immunoglobulin partner may comprise part of an immunoglobulin constant region, such as found in a Fab, or $F(ab)_2$ (i.e., a discrete part of an appropriate human constant region or framework region). Such second immunoglobulin partner may also comprise a sequence encoding an integral membrane protein exposed on the outer surface of a host cell, e.g., as part of a phage display library, or a sequence encoding a protein for analytical or diagnostic detection, e.g., horseradish peroxidase, β-galactosidase, etc.

The terms Fv, Fc, Fd, Fab, or $F(ab)_2$ are used with their standard meanings (see, e.g., Harlow et al., *Antibodies A Laboratory Manual*, Cold Spring Harbor Laboratory, (1988)).

As used herein, an "engineered antibody" describes a type of altered antibody, i.e., a full-length synthetic antibody (e.g., a chimeric or humanized antibody as opposed to an antibody fragment) in which a portion of the light and/or heavy chain variable domains of a selected acceptor antibody are replaced by analogous parts from one or more donor antibodies which have specificity for the selected epitope. For example, such molecules may include antibodies characterized by a humanized heavy chain associated with an unmodified light chain (or chimeric light chain), or vice versa. Engineered antibodies may also be characterized by alteration of the nucleic acid sequences encoding the acceptor antibody light and/or heavy variable domain framework regions in order to retain donor antibody binding specificity. These antibodies can comprise replacement of one or more CDRs (preferably all) from the acceptor antibody with CDRs from a donor antibody described herein.

A "chimeric antibody" refers to a type of engineered antibody which contains naturally-occurring variable region (light chain and heavy chains) derived from a donor antibody in association with light and heavy chain constant regions derived from an acceptor antibody.

A "humanized antibody" refers to a type of engineered antibody having its CDRs derived from a non-human donor immunoglobulin, the remaining immunoglobulin-derived parts of the molecule being derived from one (or more) human immunoglobulin(s). In addition, framework support residues may be altered to preserve binding affinity (see, e.g., Queen et al., *Proc. Natl Acad Sci USA*, 86:10029–10032 (1989), Hodgson et al., *Bio/Technology*, 9:421 (1991)).

The term "donor antibody" refers to an antibody (monoclonal, or recombinant) which contributes the nucleic acid sequences of its variable regions, CDRs, or other functional fragments or analogs thereof to a first immunoglobulin partner, so as to provide the altered immunoglobulin coding region and resulting expressed altered antibody with the antigenic specificity and neutralizing activity characteristic of the donor antibody. One donor antibody suitable for use in this invention is a non-human neutralizing monoclonal antibody (i.e., murine) designated as 2B6. The antibody 2B6 is defined as a high affinity, human-IL-5 specific (i.e., does not recognize murine IL-5), neutralizing antibody of isotype $IgG_1$ having the variable light chain DNA and amino acid sequences of SEQ ID NOs: 2 and 16, respectively, and the variable heavy chain DNA and amino acid sequences of SEQ ID NOs: 1 and 15, respectively, on a suitable murine IgG constant region.

The term "acceptor antibody" refers to an antibody (monoclonal, or recombinant) heterologous to the donor antibody, which contributes all (or any portion, but preferably all) of the nucleic acid sequences encoding its heavy and/or light chain framework regions and/or its heavy and/or light chain constant regions to the first immunoglobulin partner. Preferably a human antibody is the acceptor antibody.

"CDRs" are defined as the complementarity determining region amino acid sequences of an antibody which are the hypervariable regions of immunoglobulin heavy and light chains. See, e.g., Kabat et al., *Sequences of Proteins of Immunological Interest*, 4th Ed., U.S. Department of Health and Human Services, National Institutes of Health (1987). There are three heavy chain and three light chain CDRs (or CDR regions) in the variable portion of an immunoglobulin. Thus, "CDRs" as used herein refers to all three heavy chain CDRs, or all three light chain CDRs (or both all heavy and all light chain CDRs, if appropriate).

CDRs provide the majority of contact residues for the binding of the antibody to the antigen or epitope. CDRs of interest in this invention are derived from donor antibody variable heavy and light chain sequences, and include analogs of the naturally occurring CDRs, which analogs also share or retain the same antigen binding specificity and/or neutralizing ability as the donor antibody from which they were derived.

By 'sharing the antigen binding specificity or neutralizing ability' is meant, for example, that although mAb 2B6 may be characterized by a certain level of antigen affinity, a CDR encoded by a nucleic acid sequence of 2B6 in an appropriate structural environment may have a lower, or higher affinity. It is expected that CDRs of 2B6 in such environments will nevertheless recognize the same epitope(s) as 2B6. Exemplary heavy chain CDRs of 2B6 include SEQ ID NO: 7; SEQ ID NO: 8; SEQ ID NO: 9; and exemplary light chain CDRs of 2B6 include SEQ ID NO: 10; SEQ ID NO: 11; and SEQ ID NO: 12.

A "functional fragment" is a partial heavy or light chain variable sequence (e.g., minor deletions at the amino or carboxy terminus of the immunoglobulin variable region) which retains the same antigen binding specificity and/or neutralizing ability as the antibody from which the fragment was derived.

An "analog" is an amino acid sequence modified by at least one amino acid, wherein said modification can be chemical or a substitution or a rearrangement of a few amino acids (i.e., no more than 10), which modification permits the amino acid sequence to retain the biological characteristics, e.g., antigen specificity and high affinity, of the unmodified sequence. For example, (silent) mutations can be constructed, via substitutions, when certain endonuclease restriction sites are created within or surrounding CDR-encoding regions.

Analogs may also arise as allelic variations. An "allelic variation or modification" is an alteration in the nucleic acid sequence encoding the amino acid or peptide sequences of the invention. Such variations or modifications may be due to degeneracy in the genetic code or may be deliberately engineered to provide desired characteristics. These variations or modifications may or may not result in alterations in any encoded amino acid sequence.

The term "effector agents" refers to non-protein carrier molecules to which the altered antibodies, and/or natural or synthetic light or heavy chains of the donor antibody or other fragments of the donor antibody may be associated by conventional means. Such non-protein carriers can include conventional carriers used in the diagnostic field, e.g., polystyrene or other plastic beads, polysaccharides, e.g., as used in the BIAcore [Pharmacia] system, or other non-protein substances useful in the medical field and safe for administration to humans and animals. Other effector agents may include a macrocycle, for chelating a heavy metal atom, or radioisotopes. Such effector agents may also be useful to increase the half-life of the altered antibodies, e.g., polyethylene glycol.

II. High Affinity IL-5 Monoclonal Antibodies

For use in constructing the antibodies, altered antibodies and fragments of this invention, a non-human species (for example, bovine, ovine, monkey, chicken, rodent (e.g., murine and rat), etc.) may be employed to generate a desirable immunoglobulin upon presentment with native human IL-5 or a peptide epitope therefrom. Conventional hybridoma techniques are employed to provide a hybridoma cell line secreting a non-human mAb to IL-5. Such hybridomas are then screened for binding using IL-5 coated to 96-well plates, as described in the Examples section, or alternatively with biotinylated IL-5 bound to a streptavidin coated plate.

One exemplary, high affinity, neutralizing mAb of this instant invention is mAb 2B6, a murine antibody which can be used for the development of a chimeric or humanized antibody, described in more detail in Example 1 below. The 2B6 mAb is characterized by an antigen binding specificity for human IL-5, with a $K_d$ of less than $3.5 \times 10^{-11}$ M (about $2.2 \times 10^{-11}$ M) for-IL-5. The $K_d$ for IL-5 of a Fab fragment from 2B6 (see, Example 3H) is estimated to be about $9 \times 10^{-11}$ M as determined by optical biosensor. MAb 2B6 appears to block the binding interaction between human IL-5 and the α-chain of the human IL-5 receptor.

Another desirable donor antibody is the murine mAb, 2E3. This mAb is characterized by being isotype $IgG_{2a}$, and having a dissociation constant for hIL-5 of less than $3.5 \times 10^{-11}$ M (about $2.0 \times 10^{-11}$ M).

Yet, another desirable donor antibody is the rat mAb, 4A6. This mAb is characterized by having a dissociation constant for hIL-5 of less than $3.5 \times 10^{-11}$ M (about $1.8 \times 10^{-11}$ M). In addition, mAb 4A6 appears to block the binding interaction between human IL-5 and the β-chain of the IL-5 receptor.

This invention is not limited to the use of the 2B6 mAb, the 2E3 mAb, or its hypervariable (i.e., CDR) sequences. Any other appropriate high affinity IL-5 antibodies characterized by a dissociation constant equal or less than $3.5 \times 10^{-11}$ M for human IL-5 and corresponding anti-IL-5 CDRs may be substituted therefor. Wherever in the following description the donor antibody is identified as 2B6 or 2E3, this designation is made for illustration and simplicity of description only.

III. Antibody Fragments

The present invention also includes the use of Fab fragments or F(ab')$_2$ fragments derived from mAbs directed against human IL-5. These fragments are useful as agents protective in vivo against IL-5 and eosinophil-mediated conditions or in vitro as part of an IL-5 diagnostic. A Fab fragment contains the entire light chain and amino terminal portion of the heavy chain; and an F(ab')$_2$ fragment is the fragment formed by two Fab fragments bound by disulfide bonds. MAbs 2B6, 2E3, and other similar high affinity, IL-5 binding antibodies, provide sources of Fab fragments and F(ab')$_2$ fragments which can be obtained by conventional means, e.g., cleavage of the mAb with the appropriate proteolytic enzymes, papain and/or pepsin, or by recombinant methods. These Fab and F(ab')$_2$ fragments are useful themselves as therapeutic, prophylactic or diagnostic agents, and as donors of sequences including the variable regions and CDR sequences useful in the formation of recombinant or humanized antibodies as described herein.

The Fab and F(ab')$_2$ fragments can be constructed via a combinatorial phage library (see, e.g., Winter et al., *Ann. Rev. Immunol.*, 12:433–455 (1994)) or via immunoglobulin chain shuffling (see, e.g., Marks et al., *Bio/Technology*, 10:779–783 (1992), which are both hereby incorporated by reference in their entirety) wherein the Fd or $V_H$ immunoglobulin from a selected antibody (e.g., 2B6) is allowed to associate with a repertoire of light chain immunoglobulins, $V_L$ (or $V_K$), to form novel Fabs. Conversely, the light chain immunoglobulin from a selected antibody may be allowed to associate with a repertoire of heavy chain immunoglobulins, $V_H$ (or Fd), to form novel Fabs. Neutralizing IL-5 Fabs were obtained when the Fd of mAb 2B6 was allowed to associate with a repertoire of light chain immunoglobulins, as described in more detail in the Examples section. Hence, one is able to recover neutralizing Fabs with unique sequences (nucleotide and amino acid) from the chain shuffling technique.

IV. Anti-IL-5 Amino Acid and Nucleotide Sequences of Interest

The mAb 2B6 or other antibodies described above may contribute sequences, such as variable heavy and/or light chain peptide sequences, framework sequences, CDR sequences, functional fragments, and analogs thereof, and the nucleic acid sequences encoding them, useful in designing and obtaining various altered antibodies which are characterized by the antigen binding specificity of the donor antibody.

As one example, the present invention thus provides variable light chain and variable heavy chain sequences from the IL-5 murine antibody 2B6 and sequences derived therefrom. The heavy chain variable region of 2B6 is illustrated by FIG. 1. The CDR-encoding regions are indicated by the boxed areas and are provided in SEQ ID NO: 7; SEQ ID NO: 8; and SEQ ID NO: 9. The light chain clone variable region of 2B6 is illustrated by FIG. 2. The CDR-encoding regions are provided in SEQ ID NO: 10; SEQ ID NO: 11; and SEQ ID NO: 12.

A humanized heavy chain variable region is illustrated in FIG. 8 [SEQ ID NOs: 18 and 19]. The signal sequence is also provided in SEQ ID NO: 17. Other suitable signal sequences, known to those of skill in the art, may be substituted for the signal sequences exemplified herein. The CDR amino acid sequences of this construct are identical to the native murine and chimeric heavy chain CDRs and are provided by SEQ ID NO: 7, SEQ ID NO: 8, and SEQ ID NO: 9. An exemplary (synthetic) humanized light chain variable sequence is illustrated in FIG. 9 [SEQ ID NOs: 20 and 21].

The nucleic acid sequences of this invention, or fragments thereof, encoding the variable light chain and heavy chain peptide sequences are also useful for mutagenic introduction of specific changes within the nucleic acid sequences encoding the CDRs or framework regions, and for incorporation of the resulting modified or fusion nucleic acid sequence into a plasmid for expression. For example, silent substitutions in the nucleotide sequence of the framework and CDR-encoding regions were used to create restriction enzyme sites which facilitated insertion of mutagenized CDR (and/or framework) regions. These CDR-encoding regions were used in the construction of a humanized antibody of this invention.

Taking into account the degeneracy of the genetic code, various coding sequences may be constructed which encode the variable heavy and light chain amino acid sequences, and CDR sequences of the invention as well as functional fragments and analogs thereof which share the antigen specificity of the donor antibody. The isolated nucleic acid sequences of this invention, or fragments thereof, encoding the variable chain peptide sequences or CDRs can be used to produce altered antibodies, e.g., chimeric or humanized antibodies, or other engineered antibodies of this invention when operatively combined with a second immunoglobulin partner.

It should be noted that in addition to isolated nucleic acid sequences encoding portions of the altered antibody and antibodies described herein, other such nucleic acid sequences are encompassed by the present invention, such as those complementary to the native CDR-encoding sequences or complementary to the modified human framework regions surrounding the CDR-encoding regions. Useful DNA sequences include those sequences which hybridize under stringent hybridization conditions [see, T. Maniatis et al, *Molecular Cloning (A Laboratory Manual)*, Cold Spring Harbor Laboratory (1982), pages 387 to 389] to the DNA sequences. An example of one such stringent hybridization condition is hybridization at 4×SSC at 65° C., followed by a washing in 0.1×SSC at 65° C. for an hour. Alternatively an exemplary stringent hybridization condition is in 50% formamide, 4×SSC at 42° C. Preferably, these hybridizing DNA sequences are at least about 18 nucleotides in length, i.e., about the size of a CDR.

V. Altered immunoglobulin molecules and Altered antibodies

Altered immunoglobulin molecules can encode altered antibodies which include engineered antibodies such as chimeric antibodies and humanized antibodies. A desired altered immunoglobulin coding region contains CDR-encoding regions that encode peptides having the antigen specificity of an IL-5 antibody, preferably a high affinity antibody such as provided by the present invention, inserted into a first immunoglobulin partner (a human framework or human immunoglobulin variable region).

Preferably, the first immunoglobulin partner is operatively linked to a second immnunoglobulin partner. The second immunoglobulin partner is defined above, and may include a sequence encoding a second antibody region of interest, for example an Fc region. Second immunoglobulin partners may also include sequences encoding another immunoglobulin to which the light or heavy chain constant region is fused in frame or by means of a linker sequence. Engineered antibodies directed against functional fragments or analogs of IL-5 may be designed to elicit enhanced binding with the same antibody.

The second immunoglobulin partner may also be associated with effector 5 agents as defined above, including non-protein carrier molecules, to which the second immunoglobulin partner may be operatively linked by conventional means.

Fusion or linkage between the second immunoglobulin partners, e.g., antibody sequences, and the effector agent may be by any suitable means, e.g., by conventional covalent or ionic bonds, protein fusions, or hetero-bifunctional cross-linkers, e.g., carbodiimide, glutaraldehyde, and the like. Such techniques are known in the art and readily described in conventional chemistry and biochemistry texts.

Additionally, conventional linker sequences which simply provide for a desired amount of space between the second immunoglobulin partner and the effector agent may also be constructed into the altered immunoglobulin coding region. The design of such linkers is well known to those of skill in the art.

In addition, signal sequences for the molecules of the invention may be modified to enhance expression. As one example the 2B6 humanized antibody having the signal sequence and CDRs derived from the murine heavy chain sequence, had the original signal peptide replaced with another signal sequence [SEQ ID NO: 17].

An exemplary altered antibody contains a variable heavy and/or light chain peptide or protein sequence having the antigen specificity of mAb 2B6, e.g., the $V_H$ and $V_L$ chains. Still another desirable altered antibody of this invention is characterized by the amino acid sequence containing at least one, and preferably all of the CDRs of the variable region of the heavy and/or light chains of the murine antibody molecule 2B6 with the remaining sequences being derived from a human source, or a functional fragment or analog thereof. See, e.g., the humanized $V_H$ and $V_L$ regions (FIGS. 8 and 9).

In still a further embodiment, the engineered antibody of the invention may have attached to it an additional agent. For example, the procedure of recombinant DNA technology may be used to produce an engineered antibody of the invention in which the Fc fragment or CH2 CH3 domain of a complete antibody molecule has been replaced by an enzyme or other detectable molecule (i.e., a polypeptide effector or reporter molecule).

The second immunoglobulin partner may also be operatively linked to a non-immunoglobulin peptide, protein or fragment thereof heterologous to the CDR-containing sequence having the antigen specificity of murine 2B6. The resulting protein may exhibit both anti-IL-5 antigen specificity and characteristics of the non-immunoglobulin upon expression. That fusion partner characteristic may be, e.g., a functional characteristic such as another binding or receptor domain, or a therapeutic characteristic if the fusion partner is itself a therapeutic protein, or additional antigenic characteristics.

Another desirable protein of this invention may comprise a complete antibody molecule, having full length heavy and light chains, or any discrete fragment thereof, such as the Fab or F(ab')$_2$ fragments, a heavy chain dimer, or any minimal recombinant fragments thereof such as an Fv or a single-chain antibody (SCA) or any other molecule with the same specificity as the selected donor mAb, e.g., mAb 2B6 or 2E3. Such protein may be used in the form of an altered antibody, or may be used in its unfused form.

Whenever the second immunoglobulin partner is derived from an antibody different from the donor antibody, e.g., any isotype or class of immunoglobulin framework or constant regions, an engineered antibody results. Engineered antibodies can comprise immunoglobulin (Ig) constant regions and variable framework regions from one source, e.g., the acceptor antibody, and one or more (preferably all) CDRs from the donor antibody, e.g., the anti-IL-5 antibody described herein. In addition, alterations, e.g., deletions, substitutions, or additions, of the acceptor mAb light and/or heavy variable domain framework region at the nucleic acid or amino acid levels, or the donor CDR regions may be made in order to retain donor antibody antigen binding specificity.

Such engineered antibodies are designed to employ one (or both) of the variable heavy and/or light chains of the IL-5 mAb (optionally modified as described) or one or more of the below-identified heavy or light chain CDRs (see also FIG. 7). The engineered antibodies of the invention are neutralizing, i.e., they desirably block binding to the receptor of the IL-5 protein and they also block or prevent proliferation of IL-5 dependent cells.

Such engineered antibodies may include a humanized antibody containing the framework regions of a selected human immunoglobulin or subtype, or a chimeric antibody containing the human heavy and light chain constant regions fused to the IL-5 antibody functional fragments. A suitable human (or other animal) acceptor antibody may be one selected from a conventional database, e.g., the KABAT® database, Los Alamos database, and Swiss Protein database, by homology to the nucleotide and amino acid sequences of the donor antibody. A human antibody characterized by a homology to the framework regions of the donor antibody (on an amino acid basis) may be suitable to provide a heavy chain constant region and/or a heavy chain variable framework region for insertion of the donor CDRs. A suitable acceptor antibody capable of donating light chain constant or variable framework regions may be selected in a similar manner. It should be noted that the acceptor antibody heavy and light chains are not required to originate from the same acceptor antibody.

Desirably the heterologous framework and constant regions are selected from human immunoglobulin classes and isotypes, such as IgG (subtypes 1 through 4), IgM, IgA, and IgE. However, the acceptor antibody need not comprise only human immunoglobulin protein sequences. For instance a gene may be constructed in which a DNA sequence encoding part of a human immunoglobulin chain is fused to a DNA sequence encoding a non-immunoglobulin amino acid sequence such as a polypeptide effector or reporter molecule.

One example of a particularly desirable humanized antibody contains CDRs of 2B6 inserted onto the framework regions of a selected human antibody sequence. For neutralizing humanized antibodies, one, two or preferably three CDRs from the IL-5 antibody heavy chain and/or light chain variable regions are inserted into the framework regions of the selected human antibody sequence, replacing the native CDRs of the latter antibody.

Preferably, in a humanized antibody, the variable domains in both human heavy and light chains have been engineered by one or more CDR replacements. It is possible to use all six CDRs, or various combinations of less than the six CDRs. Preferably all six CDRs are replaced. It is possible to replace the CDRs only in the human heavy chain, using as light chain the unmodified light chain from the human acceptor antibody. Still alternatively, a compatible light chain may be selected from another human antibody by recourse to the conventional antibody databases. The remainder of the engineered antibody may be derived from any suitable acceptor human immunoglobulin.

The engineered humanized antibody thus preferably has the structure of a natural human antibody or a fragment thereof, and possesses the combination of properties required for effective therapeutic use, e.g., treatment of IL-5 mediated inflammatory diseases in man, or for diagnostic uses.

As another example, an engineered antibody may contain three CDRs of the variable light chain region of 2E3 [SEQ ID NO: 10, 11 and 13] and three CDRs of the variable heavy chain region of 2B6 [SEQ ID NO: 7, 8 and 9]. The resulting humanized antibody should be characterized by the same antigen binding specificity and high affinity of mAb 2B6.

It will be understood by those skilled in the art that an engineered antibody may be further modified by changes in variable domain amino acids without necessarily affecting the specificity and high affinity of the donor antibody (i.e., an analog). It is anticipated that heavy and light chain amino acids may be substituted by other amino acids either in the variable domain frameworks or CDRs or both.

In addition, the constant region may be altered to enhance or decrease selective properties of the molecules of the instant invention. For example, dimerization, binding to Fc receptors, or the ability to bind and activate complement (see, e.g., Angal et al., *Mol. Immunol*, 30:105–108 (1993), Xu et al., *J. Biol. Chem*, 269:3469–3474 (1994), Winter et al., EP 307,434-B).

An altered antibody which is a chimeric antibody differs from the humanized antibodies described above by providing the entire non-human donor antibody heavy chain and light chain variable regions, including framework regions, in association with human immunoglobulin constant regions for both chains. It is anticipated that chimeric antibodies which retain additional non-human sequence relative to humanized antibodies of this invention may elicit a significant immune response in humans.

Such antibodies are useful in the prevention and treatment of IL-5 mediated disorders, as discussed below.

VI. Production of Altered Antibodies and Engineered Antibodies

Preferably, the variable light and/or heavy chain sequences and the CDRs of mAb 2B6 or other suitable donor mAbs (e.g., 2E3, 2F2, 4A6, etc.), and their encoding nucleic acid sequences, are utilized in the construction of altered antibodies, preferably humanized antibodies, of this invention, by the following process. The same or similar techniques may also be employed to generate other embodiments of this invention.

A hybridoma producing a selected donor mAb, e.g., the murine antibody 2B6, is conventionally cloned, and the DNA of its heavy and light chain variable regions obtained by techniques known to one of skill in the art, e.g., the techniques described in Sambrook et al., (*Molecular Cloning (A Laboratory Manual*), 2nd edition, Cold Spring Harbor Laboratory (1989)). The variable heavy and light regions of 2B6 containing at least the CDR-encoding regions and those portions of the acceptor mAb light and/or heavy variable domain framework regions required in order to retain donor mAb binding specificity, as well as the remaining immunoglobulin-derived parts of the antibody chain derived from a human immunoglobulin are obtained using polynucleotide primers and reverse transcriptase. The CDR-encoding regions are identified using a known database and by comparison to other antibodies.

A mouse/human chimeric antibody may then be prepared and assayed for binding ability. Such a chimeric antibody contains the entire non-human donor antibody $V_H$ and $V_L$ regions, in association with human Ig constant regions for both chains.

Homologous framework regions of a heavy chain variable region from a human antibody were identified using computerized databases, e.g., KABAT®, and a human antibody having homology to 2B6 was selected as the acceptor antibody. The sequences of synthetic heavy chain variable regions containing the 2B6 CDR-encoding regions within the human antibody frameworks were designed with optional nucleotide replacements in the framework regions to incorporate restriction sites. This designed sequence was then synthesized using long synthetic oligomers. Alternatively, the designed sequence can be synthesized by overlapping oligonucleotides, amplified by polymerase chain reaction (PCR), and corrected for errors.

A suitable light chain variable framework region was designed in a similar manner.

A humanized antibody may be derived from the chimeric antibody, or preferably, made synthetically by inserting the donor mAb CDR-encoding regions from the heavy and light chains appropriately within the selected heavy and light chain framework. Alternatively, a humanized antibody of the invention made be prepared using standard mutagenesis techniques. Thus, the resulting humanized antibody contains human framework regions and donor mAb CDR-encoding regions. There may be subsequent manipulation of framework residues. The resulting humanized antibody can be expressed in recombinant host cells, e.g., COS, CHO or myeloma cells. Other humanized antibodies may be prepared using this technique on other suitable IL-5-specific, neutralizing, high affinity, non-human antibodies.

A conventional expression vector or recombinant plasmid is produced by placing these coding sequences for the altered antibody in operative association with conventional regulatory control sequences capable of controlling the replication and expression in, and/or secretion from, a host cell. Regulatory sequences include promoter sequences, e.g., CMV promoter, and signal sequences, which can be derived from other known antibodies. Similarly, a second expression vector can be produced having a DNA sequence which encodes a complementary antibody light or heavy chain. Preferably this second expression vector is identical to the first except insofar as the coding sequences and selectable markers are concerned, so to ensure as far as possible that each polypeptide chain is functionally expressed. Alternatively, the heavy and light chain coding sequences for the altered antibody may reside on a single vector.

A selected host cell is co-transfected by conventional techniques with both the first and second vectors (or simply transfected by a single vector) to create the transfected host cell of the invention comprising both the recombinant or synthetic light and heavy chains. The transfected cell is then cultured by conventional techniques to produce the engineered antibody of the invention. The humanized antibody which includes the association of both the recombinant heavy chain and/or light chain is screened from culture by appropriate assay, such as ELISA or RIA. Similar conventional techniques may be employed to construct other altered antibodies and molecules of this invention.

Suitable vectors for the cloning and subcloning steps employed in the methods and construction of the compositions of this invention may be selected by one of skill in the art. For example, the conventional pUC series of cloning vectors, may be used. One vector used is pUC19, which is commercially available from supply houses, such as Amersham (Buckinghamshire, United Kingdom) or Pharmacia (Uppsala, Sweden). Additionally, any vector which is capable of replicating readily, has an abundance of cloning sites and selectable genes (e.g., antibiotic resistance), and is easily manipulated may be used for cloning. Thus, the selection of the cloning vector is not a limiting factor in this invention.

Similarly, the vectors employed for expression of the engineered antibodies according to this invention may be selected by one of skill in the art from any conventional vector. The vectors also contain selected regulatory sequences (such as CMV promoters) which direct the replication and expression of heterologous DNA sequences in selected host cells. These vectors contain the above described DNA sequences which code for the engineered antibody or altered immunoglobulin coding region. In addition, the vectors may incorporate the selected immunoglobulin sequences modified by the insertion of desirable restriction sites for ready manipulation.

The expression vectors may also be characterized by genes suitable for amplifying expression of the heterologous DNA sequences, e.g., the mammalian dihydrofolate reductase gene (DHFR). Other preferable vector sequences include a poly A signal sequence, such as from bovine growth hormone (BGH) and the betaglobin promoter sequence (betaglopro). The expression vectors useful herein may be synthesized by techniques well known to those skilled in this art.

The components of such vectors, e.g. replicons, selection genes, enhancers, promoters, signal sequences and the like, may be obtained from commercial or natural sources or synthesized by known procedures for use in directing the expression and/or secretion of the product of the recombinant DNA in a selected host. Other appropriate expression vectors of which numerous types are known in the art for mammalian, bacterial, insect, yeast, and fungal expression may also be selected for this purpose.

The present invention also encompasses a cell line transfected with a recombinant plasmid containing the coding sequences of the engineered antibodies or altered immunoglobulin molecules thereof. Host cells useful for the cloning and other manipulations of these cloning vectors are also conventional. However, most desirably, cells from various strains of E. coli are used for replication of the cloning vectors and other steps in the construction of altered antibodies of this invention.

Suitable host cells or cell lines for the expression of the engineered antibody or altered antibody of the invention are preferably mammalian cells such as CHO, COS, a fibroblast cell (e.g., 3T3), and myeloid cells, and more preferably a CHO or a myeloid cell. Human cells may be used, thus enabling the molecule to be modified with human glycosylation patterns. Alternatively, other eukaryotic cell lines may be employed. The selection of suitable mammalian host cells and methods for transformation, culture, amplification, screening and product production and purification are known in the art. See, e.g., Sambrook et al., cited above.

Bacterial cells may prove useful as host cells suitable for the expression of the recombinant Fabs of the present invention (see, e.g., Plückthun, A., *Immunol. Rev.*, 130:151–188 (1992)). However, due to the tendency of proteins expressed in bacterial cells to be in an unfolded or improperly folded form or in a non-glycosylated form, any recombinant Fab produced in a bacterial cell would have to be screened for retention of antigen binding ability. If the molecule expressed by the bacterial cell was produced in a properly folded form, that bacterial cell would be a desirable host. For example, various strains of *E. coli* used for expression are well-known as host cells in the field of biotechnology. Various strains of *B. subtilis*, Streptomyces, other bacilli and the like may also be employed in this method.

Where desired, strains of yeast cells known to those skilled in the art are also available as host cells, as well as insect cells, e.g. Drosophila and Lepidoptera and viral expression systems. See, e.g. Miller et al., *Genetic Engineering*, 8:277–298, Plenum Press (1986) and references cited therein.

The general methods by which the vectors of the invention may be constructed, the transfection methods required to produce the host cells of the invention, and culture methods necessary to produce the altered antibody of the invention from such host cell are all conventional techniques. Likewise, once produced, the altered antibodies of the invention may be purified from the cell culture contents according to standard procedures of the art, including ammonium sulfate precipitation, affinity columns, column chromatography, gel electrophoresis and the like. Such techniques are within the skill of the art and do not limit this invention.

Yet another method of expression of the humanized antibodies may utilize expression in a transgenic animal, such as described in U.S. Pat. No. 4,873,316. This relates to an expression system using the animal's casein promoter which when transgenically incorporated into a mammal permits the female to produce the desired recombinant protein in its milk.

Once expressed by the desired method, the engineered antibody is then examined for in vitro activity by use of an appropriate assay. Presently conventional ELISA assay formats are employed to assess qualitative and quantitative binding of the engineered antibody to IL-5. Additionally, other in vitro assays may also be used to verify neutralizing efficacy prior to subsequent human clinical studies performed to evaluate the persistence of the engineered antibody in the body despite the usual clearance mechanisms.

Following the procedures described for humanized antibodies prepared from 2B6, one of skill in the art may also construct humanized antibodies from other donor IL-5 antibodies, variable region sequences and CDR peptides described herein. Engineered antibodies can be produced with variable region frameworks potentially recognized as "self" by recipients of the engineered antibody. Minor modifications to the variable region frameworks can be implemented to effect large increases in antigen binding without appreciable increased immunogenicity for the recipient. Such engineered antibodies may effectively treat a human for IL-5 mediated conditions. Such antibodies may also be useful in the diagnosis of such conditions.

VII. Therapeutic/Prophylactic Uses

This invention also relates to a method of treating humans experiencing eosinophilia-related symptoms, such as asthma, which comprises administering an effective dose of antibodies including one or more of the engineered antibodies or altered antibodies described herein, or fragments thereof.

The therapeutic response induced by the use of the molecules of this invention is produced by the binding to human IL-5 and thus subsequently blocking eosinophil stimulation. Thus, the molecules of the present invention, when in preparations and formulations appropriate for therapeutic use, are highly desirable for those persons experiencing an allergic and/or atopic response, or a response associated with eosinophilia, such as but not limited to, allergic rhinitis, asthma, chronic eosinophilic pneumonia, allergic bronchopulmonary aspergillosis, coeliac disease, eosinophilic gastroenteritis, Churg-Strauss syndrome (periarteritis nodosa plus atopy), eosinophilic myalgia syndrome, hypereosinophilic syndrome, oedematous reactions including episodic angiodema, helminth infections, where eosinophils may have a protective role, onchocercal dermatitis and atopic dermatitis.

The altered antibodies, antibodies and fragments thereof of this invention may also be used in conjunction with other antibodies, particularly human mAbs reactive with other markers (epitopes) responsible for the condition against which the engineered antibody of the invention is directed.

The therapeutic agents of this invention are believed to be desirable for treatment of allergic conditions from about 2 days to about 3 weeks, or as needed. For example, longer treatments may be desirable when treating seasonal rhinitis or the like. This represents a considerable advance over the currently used infusion protocol with prior art treatments of IL-5 mediated disorders. The dose and duration of treatment relates to the relative duration of the molecules of the present invention in the human circulation, and can be adjusted by one of skill in the art depending upon the condition being treated and the general health of the patient.

The mode of administration of the therapeutic agent of the invention may be any suitable route which delivers the agent to the host. The altered antibodies, antibodies, engineered antibodies, and fragments thereof, and pharmaceutical compositions of the invention are particularly useful for parenteral administration, i.e., subcutaneously, intramuscularly, intravenously, or intranasally.

Therapeutic agents of the invention may be prepared as pharmaceutical compositions containing an effective amount of the engineered (e.g., humanized) antibody of the invention as an active ingredient in a pharmaceutically acceptable carrier. In the prophylactic agent of the invention, an aqueous suspension or solution containing the engineered antibody, preferably buffered at physiological pH, in a form ready for injection is preferred. The compositions for parenteral administration will commonly comprise a solution of the engineered antibody of the invention or a cocktail thereof dissolved in an pharmaceutically acceptable carrier, preferably an aqueous carrier. A variety of aqueous carriers may be employed, e.g., 0.4% saline, 0.3% glycine, and the like. These solutions are sterile and generally free of particulate matter. These solutions may be sterilized by conventional, well known sterilization techniques (e.g., filtration). The compositions may contain pharmaceutically acceptable auxiliary substances as required to approximate physiological conditions such as pH adjusting and buffering agents, etc. The concentration of the antibody of the invention in such pharmaceutical formulation can vary widely, i.e., from less than about 0.5%, usually at or at least about 1% to as much as 15 or 20% by weight and will be selected primarily based on fluid volumes, viscosities, etc., according to the particular mode of administration selected.

Thus, a pharmaceutical composition of the invention for intramuscular injection could be prepared to contain 1 mL sterile buffered water, and between about 1 ng to about 100 mg, e.g. about 50 ng to about 30 mg or more preferably, about 5 mg to about 25 mg, of an engineered antibody of the invention. Similarly, a pharmaceutical composition of the invention for intravenous infusion could be made up to contain about 250 ml of sterile Ringer's solution, and about 1 to about 30 and preferably 5 mg to about 25 mg of an engineered antibody of the invention. Actual methods for preparing parenterally administrable compositions are well known or will be apparent to those skilled in the art and are described in more detail in, for example, Remington's Pharmaceutical Science, 15th ed., Mack Publishing Company, Easton, Pa.

It is preferred that the therapeutic agent of the invention, when in a pharmaceutical preparation, be present in unit dose forms. The appropriate therapeutically effective dose can be determined readily by those of skill in the art. To effectively treat an inflammatory disorder in a human or other animal, one dose of approximately 0.1 mg to approximately 20 mg per 70 kg body weight of a protein or an antibody of this invention should be administered parenterally, preferably i.v. or i.m. (intramuscularly). Such dose may, if necessary, be repeated at appropriate time intervals selected as appropriate by a physician during the inflammatory response.

The altered antibodies and engineered antibodies of this invention may also be used in diagnostic regimens, such as for the determination of L-5 mediated disorders or tracking progress of treatment of such disorders. As diagnostic reagents, these altered antibodies may be conventionally labeled for use in ELISA's and other conventional assay formats for the measurement of IL-5 levels in serum, plasma or other appropriate tissue, or the release by human cells in culture. The nature of the assay in which the altered antibodies are used are conventional and do not limit this disclosure.

Thus, one embodiment of the present invention relates to a method for aiding the diagnosis of allergies and other conditions associated with excess eosinophil production in a patient which comprises the steps of determining the amount of human IL-5 in sample (plasma or tissue) obtained from said patient and comparing said determined amount to the mean amount of human IL-5 in the normal population, whereby the presence of a significantly elevated amount of IL-5 in the patient's sample is an indication of allergies and other conditions associated with excess eosinophil production.

The antibodies, altered antibodies or fragments thereof described herein can be lyophilized for storage and reconstituted in a suitable carrier prior to use. This technique has been shown to be effective with conventional immunoglobulins and art-known lyophilization and reconstitution techniques can be employed.

The following examples illustrate various aspects of this invention including the construction of exemplary engineered antibodies and expression thereof in suitable vectors and host cells, and are not to be construed as limiting the scope of this invention. All amino acids are identified by conventional three letter or single letter codes. All necessary restriction enzymes, plasmids, and other reagents and materials were obtained from commercial sources unless otherwise indicated. All general cloning ligation and other recombinant DNA methodology were as performed in T. Maniatis et al., cited above, or the second edition thereof (1989), eds. Sambrook et al., by the same publisher ("Sambrook et al.").

EXAMPLE 1

Production of MAbs to hIL-5

Human IL-5 was expressed in Drosophila Schneider 2 (S2) cells and purified to homogeneity. Murine IL-5 was expressed in Baculovirus using *Spodoptera frugiperda* 21 (Sf21) cells and purified to homogeneity. Monoclonal antibody TRFK-5 (a neutralizing rat anti-mouse IL-5 antibody) was obtained from Genzyme Corp. (Cambridge, Mass.).

A. Immunization Procedure:

Recombinant human IL-5 (IL-5) was used as the immunogen for a panel of seven CAF1 female mice (Charles River, Wilmington, Mass.). The animals received three subcutaneous injections of IL-5 in phosphate buffered saline (PBS) emulsified with a one to one ratio of TiterMAX™ (CytoRx Corp., Norcross, Ga.) over a period of four months. The priming antigen dose was 50 μg (micrograms) and boosts were 25 and 10 μg (micrograms). After the boosts, serum samples were collected and assayed both for binding to IL-5 and for neutralization activity via the receptor binding inhibition assay and B13 proliferation assay (or IL-5 neutralization assay (Example 2C)). All of the mice produced serum samples that bound to IL-5. Animals selected as spleen donors were boosted intravenously with 10 μg (micrograms) of recombinant human IL-5 three days prior to euthanasia.

B. Hybridoma Development:

The fusion procedure, first reported by Kohler et al., (*Nature*, 256:495 (1975)), was used with modifications to perform the technique using a cell monolayer (Kennet et al., Eds., "Hybridomas: A new dimension in biological analysis", pp. 368–377, Plenum Press, New York). Spleen cells from two donor mice were pooled and fusions performed using a ratio of 50 million spleen cells to ten million SP2/0/Ag14 myeloma cells. Supernatants from fusion-positive wells were assayed for binding to IL-5 by ELISA. Wells containing cells producing antibody to IL-5 were expanded and supernatants screened in an IL-5 receptor binding inhibition assay, and a B 13 (neutralization) proliferation assay (described below).

Sixteen hybridomas were isolated which secreted mAbs reactive with IL-5. The hybridoma supernatants were mixed with iodinated IL-5, added to a membrane extract prepared from Drosophila cells expressing the α-chain of the IL-5 receptor (IL-5R), and assayed for inhibition of receptor binding. Eleven of the hybridoma supernatants inhibited by greater than 60% the binding of iodinated IL-5 to the IL-5 receptor α-chain. Three of the mAbs, 2B6, 2E3 and 2F2, also inhibited by greater than 70% the proliferation of murine B 13 cells in response to human but not murine IL-5. Five of the hybridomas, four of which blocked binding and/or proliferation (1C6, 2B6, 2E3 and 2F2) and 1 of which was non-neutralizing (24G9), were repeatedly subcloned in soft agar to generate stable clonal cell lines. Supernatants from the cloned lines were screened for cross-reactivity by ELISA and did not bind to human IL-1α, IL-1β, IL-4, IL-8, M-CSF or TGFα. The mAbs were purified and binding affinities were estimated from optical biosensor (BlAcore) analysis to range from 10 to 100 pM. Supernatants from the lines were isotyped using murine isotyping reagents (PharMingen, San Diego, Calif.). A summary of the affinities and $IC_{50}$ for neutralizing activities of the mAbs is presented in Table 1 (Example 2).

By similar methods, rat hybridomas were derived from immunized rats, using a comparable immunization protocol and rat myelomas for the fusion as described for the mouse. Two rat hybridomas, 4A6 and 5D3, were identified that produced mAbs which bound to L-5. Like mAbs 2B6, 2E3 and 2F2, mAbs 4A6 and 5D3 were found to be neutralizing in the B 13 assay described below.

C. Hybridoma Deposit:

The hybridoma cell line SK119-2B6.206.75(1) producing monoclonal antibody 2B6 was deposited on December 21, 1994 with the American Type Culture Collection (ATCC), 10801 University Boulevard, Manassas, Va. 20110-2209, USA, under accession number HB 11783, and has been accepted as a patent deposit, in accordance with the Budapest Treaty of 1977 governing the deposit of microorganisms for the purposes of patent procedures.

The hybridoma cell line SK119-2E3.39.40.2 producing monoclonal antibody 2E3 was deposited on Dec. 21, 1994 with the American Type Culture Collection (ATCC), 10801 University Boulevard, Manassas, Va. 20110–2209, USA, under accession number HB 11782, and has been accepted as a patent deposit, in accordance with the Budapest Treaty of 1977 governing the deposit of microorganisms for the purposes of patent procedures.

The hybridoma cell line SK119–2F2.37.80.12 producing monoclonal antibody 2F2 was deposited on Dec. 21, 1994 with the American Type Culture Collection (ATCC), 10801 University Boulevard, Manassas, Va. 20110-2209, USA, under accession number HB 11781, and has been accepted as a patent deposit, in accordance with the Budapest Treaty of 1977 governing the deposit of microorganisms for the purposes of patent procedures.

The hybridoma cell line SK119–24G9.8.20.5 producing monoclonal antibody 24G9 was deposited on Dec. 21, 1994 with the American Type Culture Collection (ATCC), 10801 University Boulevard, Manassas, Va. 20110-2209, USA, under accession number HB 11780, and has been accepted as a patent deposit, in accordance with the Budapest Treaty of 1977 governing the deposit of microorganisms for the purposes of patent procedures.

The hybridoma cell line 4A6(1)G1F7 producing monoclonal antibody 4A6 was deposited on Jun. 8, 1995 with the American Type Culture Collection (ATCC), 10801 University Boulevard, Manassas, Va. 20110-2209, USA, under accession number HB 11943, and has been accepted as a patent deposit, in accordance with the Budapest Treaty of 1977 governing the deposit of microorganisms for the purposes of patent procedures.

The hybridoma cell line 5D3(1)F5D6 producing monoclonal antibody 5D3 was deposited on June 8, 1995 with the American Type Culture Collection (ATCC), 10801 University Boulevard, Manassas, Va. 20110-2209, USA, under accession number HB 11942, and has been accepted as a patent deposit, in accordance with the Budapest Treaty of 1977 governing the deposit of microorganisms for the purposes of patent procedures.

EXAMPLE 2

Assays

A. ELISA:

Individual wells of MaxiSorb™ immuno plates (Nunc, Naperville, Ill.) were coated with 0.2 ug IL-5 in 0.05M carbonate buffer pH 9.6. After incubating overnight at 4° C., the plates were rinsed with PBS containing 0.025% Tween® 20, and blocked with 1% BSA in PBS with 0.025% Tween® 20 for two hours at room temperature. Undiluted hybrid supernatants were added to the IL-5 coated wells and incubated at room temperature for two hours. After the plates were rinsed, peroxidase labeled goat anti-mouse IgG & IgM (Boehringer Mannheim, Indianapolis, In) was added at 1/7500 dilution in PBS containing 1% BSA and 0.025% Tween® 20. Two hours later the plates were washed and 0.2 ml of 0.1M citrate buffer pH 4.75 containing 0.1% urea peroxide and 1 mg/ml orthophenylenediamine was added. After 15 min the plates were read at 450nm on a VMax™ Microplate Reader (Molecular Devices, Menlo Park, Calif.).

B. Receptor Binding Inhibition Assay:

Membrane extracts of Drosophila S2 cells expressing the α-chain of the human IL-5 Receptor (IL-5R) were used to measure the effect of antibody on IL-5 binding to receptor. To prepare the membranes, $10^9$ cells were pelleted at 1000×g at 4° C. for 10 min. The cell pellet was frozen in a dry ice/ethanol bath for 15 min. The pellet was thawed, resuspended in 10 ml PBS at 4° C. and pelleted at 1000×g for 10 min. The cell pellet was washed 2× in PBS and resuspended in 13.5 ml Hypotonic buffer (10 mM Tris pH 7.5, 3 mM $MgCl_2$, 1 mM dithiothreitol, 1 mM phenylmethylsulfonyl fluoride, 1 uM leupeptin, 1 uM pepstatin A) and incubated on ice for 5 min. The cell suspension was homogenized in a 15 ml Dounce homogenizer and brought to a final concentration of 0.25 M sucrose with a solution of 2.5 M sucrose. Cell debris was removed by a 15 min centrifugation at 1000×g. Cell membranes were pelleted at 100,000×g at 4° C. for 90 min and resuspended in 50 ml of 10 mM Tris pH 7.5, 3 mM $MgCl_2$, 250 mM sucrose, and stored at −70° C.

Assays with Drosophila membranes containing receptor were performed in MultiscreenGV™ plates (Millipore Corp., Bedford, Mass.) using Drosophila tissue culture medium M3 (Lindquist et al., *Drosophila Inf. Serv.*, 58: 163 (1982)) containing 25 mM HEPES buffer pH 7.2 and 0.1% BSA (Binding Buffer). Wells were pre-blocked with 0.1 ml binding buffer. 50 ul of the test sample, in triplicate, was added to wells followed by 25 ul iodinated ($^{125}I$) IL-5. After 20 minutes incubation at room temperature, 25 ul of the membrane extract of Drosophila S2 cells expressing the α-chain of the human IL5R was added to the wells. After 1 hour further incubation the membranes were collected by vacuum filtration and washed 3× with binding buffer. Filters were dried and counted.

C. IL-5 Neutralization Assay:

The murine IL-5/IL-3 dependent cell line LyH7.B13 (B13) was obtained courtesy of R. Palacios, Basel Institute of Immunology, Switzerland. Cells were subcultured twice weekly in RPMI 1640 medium (GibcoBRL, Renfrewshire, UK), supplemented with L-Glutamine, non-essential amino acids, sodium pyruvate, penicillin-streptomycin (all GibcoBRL), plus 2-mercaptoethanol ($5 \times 10^{-5}$ M, Sigma), 10% fetal bovine serum (Globepharm, Surrey, UK) and 1–10 units murine IL-5. For assays, cells were cultured for 48 hours in triplicate (5000 cells/well) in 96-well round bottom plates in the presence of appropriately diluted test samples and pulsed with 0.5 uCi $^3H$-thymidine (Amersham, Bucks, UK) for the final 4 hours. They were processed for scintillation counting in a 1205 Betaplate (LKB Wallac, Beds, UK)

D. Optical Biosensor:

Kinetic and equilibrium binding properties with immobilized hIL-5 and antibodies were measured using a BIAcore optical biosensor (Pharmacia Biosensor, Uppsala, Sweden). Kinetic data were evaluated using relationships described previously (Karlsson et al., *J. Immunol. Meth.*, 145:229–240 (1991)) and which is incorporated by reference in its entirety.

Three of the neutralizing mAbs, namely 2B6, 2E3 and 2F2, had very similar potencies of inhibition of $^{125}I$-IL-5 binding to membrane receptor and neutralization of B cell proliferation and also very similar affinities for IL-5 (see Table I). The nucleotide sequences of the $V_H$ and $V_L$ from these three mAbs, 2 IgG 1 and 1 IgG2a, respectively, were determined. The sequences obtained were very similar, differing only at a few residues.

TABLE I

Affinity and neutralizing activity of mAbs reactive with human IL-5

| mAb | KD (pM)[a] | Binding IC$_{50}$ (nM)[b] | Neutralization Proliferation IC$_{50}$[c] | 100% Inhibition[c] |
|---|---|---|---|---|
| 2B6 | 22 | 1 | 70 | 200 |
| 2E3 | 20 | 1 | 90 | 600 |
| 2F2 | 13 | 1 | 150 | 340 |
| 1C6 | 86 | 43 | 12,200 | ND |
| 24G9 | ND | >133 | >100,000 | ND |
| 4A6 | 18 | >88 | 28 | 100 |
| 5D3 | ND | ND | 100 | 10,000 |

[a]Determined by optical biosensor (BIAcore) analysis (25° C.)
[b]Inhibition of $^{125}$I-IL-5 binding to IL-5R (α chain) from Drosophila membranes
[c]Inhibition of proliferation (in pM) of B13 cells in response to 8 pM human IL-5
ND = No data

EXAMPLE 3

Isolation and Characterization of IL-5 Fabs from Combinatorial Library

A. PCR and Combinatorial Library Construction:

RNA purified from the spleens of three mice was reverse transcribed with a cDNA kit (Boehringer Mannheim, Indianapolis, Ind.) using either the primer (dT)$_{15}$ supplied with the kit or the 3' Fd (IgG1, IgG2a & IgG3) and kappa light chain primers as described by Huse et al. (*Science*, 246:1275 (1989)) and Kang, S. A. (*Methods: Companion Methods Enzymol.*, 2:111 (1991)) which are hereby incorporated by reference in their entirety. Immunoglobulin cDNAs were amplified by PCR using the primers and the thermal cycling conditions described (Huse et al. supra). The Hot Start technique using AmpliWax™ PCR Gem 100 (Perkin Elmer Cetus, Norwalk, Conn.) beads and the manufacturer's protocol was used for all of the reactions. The PCR products were gel purified, digested, and ligated into the pMKFabGene3 vector (Ames et al., *J. Immunol.*, 152:4572 (1994)). The library titer following ligation with the Fd cDNAs was 5.1×10$^7$ CFU and following ligation with the kappa cDNAs was 1.5×10$^6$ CFU. XLI-Blue cells (Stratagene, La Jolla, Calif.) transformed with the phagemid library were infected with helper phage VCSM13 (Stratagene) and phage were prepared as described by Barbas and Lerner (*Methods: Companion Methods Enzymol.*, 2:119 (1991)).

B. Biopanning:

Four microtiter wells (Immulon II Removawell Strips, Dynatech Laboratories Inc., Chantilly, Va.) were coated overnight at 40C with IL-5 (1ug/well) in 0.1M bicarbonate, pH 8.6. The wells were washed with water and blocked with PBS containing 3% BSA at 37+ C. for 1 hour. The blocking solution was removed, and the library was added to microtiter wells (50 ul/well) and incubated at 37+ C. for 2 hours. Wells were washed 10 times with TBS/Tween® (50 mM Tris-HCl, pH 7.5, 150 mM NaCl, 0.5% Tween® 20) and once with H$_2$O prior to elution of the adherent phage with 0.1 M HCl, adjusted to pH 2.2 with glycine, containing 1 mg/ml BSA.

C. Colony Lifts:

Colony lifts from clones isolated from the third and fourth rounds of biopanning were processed as described (Barbas and Lerner, supra). Filters were incubated for 1 hour at room temperature with 0.5–1.0 uCi $^{125}$I-IL-5, which had been iodinated using Bolton-Hunter reagent (NEN, Billerica, Mass.) following the manufacturers recommended procedure, in PBS containing 1% BSA, washed with PBS 0.25% Tween, and exposed to Kodak XAR film. Colonies expressing IL-5-reactive Fabs were detected by autoradiography.

D. Preparation of Soluble FABs:

Phagemid DNAs were digested with NheI and SpeI to remove gene III and self-ligated. XL1-Blue cells were transformed, and isolated clones were grown overnight at 37° C. in 5.0 ml super broth (SB) medium (30 g tryptone, 20 g yeast extract, 10 g 3-[N-Morpholino]propanesulfonic acid, MOPS with pH adjusted to 7) containing 1% glucose and 50 ug/ml carbenicillin. Cells from 1 ml of this culture were pelleted at 3500 rpm for 10 min in Beckman GS-6R centrifuge and used to inoculate 5 ml SB containing 50 ug/ml carbenicillin. Cultures were shaken for 1 hour at 37° C., Isopopyl-b-D-thiogalactopyranoside (IPTG; 1 mM) was added and the cultures were transferred to 28° C. overnight. Soluble Fab was prepared from periplasmic extracts by lysing the cell pellet for 20 min at 4° C. in 20% sucrose suspended in 30 mM Tris pH 8.0, followed by centrifugation in a Microfuge for 10 min. Fab concentrations were estimated by western blot by comparison to samples containing known amounts of murine Fab. The different bacterial periplasmic extracts contained similar concentrations of Fab, ranging from 1 to 20 ug/ml, as estimated by western blot analysis.

E. Purification of FABs:

A chelating peptide was engineered onto the carboxy-terminal end of the heavy chain to aid in protein purification. Following removal of the M13 geneIII coding region, via digestion with NheI and SpeI, a pair of overlapping oligonucleotides: [SEQ ID NO: 43] 5'-CTAGCCACCACCACCACCACCACTAA-3'; [SEQ ID NO: 44] 3'-GGTGGTGGTGGTGGTGGTGATTGATC-5' encoding six histidine residues were subcloned into the Fab expression vector. Induction of Fab expression was performed as described above. Following overnight induction at 28° C. periplasmic lysate of the cell pellet was prepared by 30 min incubation at 4° C. in 20% sucrose, 30 mM TRIS pH 8.0. Urea and Brij-35 detergent were added to the clarified supernatant to final concentrations of 2M and 1% respectively. After stirring at room temperature for 1 hour, the treated and clarified supernatant was loaded at 0.5 ml/min directly onto a 5 ml Nickel-NTA metal chelating column (1.5×3 cm) equilibrated with buffer A (100 mM Na-Phosphate, 10 mM Tris, 0.3 M NaCl, 2 M urea, pH 8.0). After a 4 column volume (20 ml) wash bound materials were eluted with a 6 column volume (30 ml) reverse pH gradient from pH 8 to pH 4 in the same buffer as above. The purified Fabs eluted from the column in a sharp symmetrical peak at pH 5.5. They were >90% pure and free of DNA.

F. FAB ELISA:

Immnulon II plates (Dynatech) were coated overnight at 4° C. with protein suspended (1 mg/ml; 50 ml per well) in 0.1 M bicarbonate buffer, pH 8.6. Dilutions and washes were performed in PBS containing 0.05% Tween™ 20. Plates were washed and blocked for 1 hour with PBS containing 1% BSA at room temperature. Various dilutions of the bacterial supernatants containing soluble Fabs, or purified Fabs, were added to the plates. Following a one hour incubation plates were washed and biotinylated goat anti-mouse kappa (Southern Biotechnology Associates, Inc., Birmingham, Ala.) was added (1:2000 dilution; 50 ul/well) for 1 hour. The plates were washed and streptavidin labeled horseradish peroxidase was added (1:2000 dilution; 50 ul/well) for 1 hour. The plates were washed, ABTS peroxidase substrate was added (100 ul/well; Kirkegaard & Perry Laboratories, Gaithersburg, Md.) and the optical density at 405 nm was read on a UVmax™ (Molecular Devices) microplate reader.

G. Isolation and Characterization of Fabs from a Combinatorial Library:

Phage bearing Fabs to IL-5 were selected from the library by multiple rounds of biopanning against microtiter wells coated with IL-5. After 4 rounds of selection IL-5 reactive Fabs were identified by a colony lift assay using $^{125}$I-IL-5. Thirty four colonies from the third round and 4 colonies from the fourth round were identified which bound labeled IL-5. Binding to IL-5 was confirmed by direct binding ELISA using culture supernatants expressing the Fab-geneIII fusion protein. DNA was isolated from these colonies and, after removing the coding region of M13 gene III, soluble Fab expression was induced. Periplasmic fractions were prepared and assayed by ELISA for binding to IL-5. The Fabs bound specifically to IL-5 with no demonstrable binding to an another protein, rC5a.

The undiluted periplasmic extracts (containing 1 to 20 ug/ml Fab) were assayed in the IL-5R binding inhibition assay (Example 2). None of the Fabs inhibited binding of iodinated IL-5 to the IL-5Rα by more than 35%.

H. Conversion of Neutralizing mAb to a FAB:

The Fd and κ cDNAs of mAb (2B6) were isolated by PCR using the conditions described above. The gel-purified fragments were subcloned into the pMKFabGene3 vector which had been modified to include the hexa-His sequence 3' of the gene III cDNA, resulting in the plasmid pMKFabGene3H. A functional, IL-5 binding Fab clone containing the 2B6 heavy and light chains was identified by a colony lift assay. Upon removal gene III via Nhe I/SpeI I digestion and self-ligation the heavy chain was fused in frame to the hexa-His, allowing purification as described above. In a dose dependent manner, this Fab inhibited receptor binding with an IC50 of approximately 7.5 ug/ml, similar to that of the parent mAb, murine 2B6.

I. Construction and Screening of Chain-Shuffled Library:

The cDNA encoding the Fd of the neutralizing mAb 2B6 was subcloned as an XhoI/SpeI fragment into pMKFabGene3H which contained a SstI/XbaI fragment in lieu of a light chain cDNA. This phagemid was digested with SstI and XbaI and ligated with the SstI/XbaI digested light chain PCR product derived from the IL-5 immunized mice (described above). The library titer following ligation was 4×10⁵ CFU. Biopanning, and colony lift assay was performed as described above for the combinatorial library.

The library was constructed by pairing the cDNA encoding the Fd of the neutralizing mAb 2B6 with the same light chain repertoire, recovered from the IL-5 immunized mice, used to generate the combinatorial library. This chain shuffled library was subjected to 4 rounds of biopanning vs immobilized IL-5 and the resultant colonies were assayed for IL-5 reactivity using the colony lift assay. Positive colonies, which bound iodinated IL-5, were further assayed by ELISA and the IL-5Rα binding assay. Two of the Fabs, 2 & 15, recovered from the chain shuffled library blocked binding of IL-5 to the IL-5Rα and inhibited IL-5 dependent proliferation in the B13 assay. The sequences of these 2 Vks were similar to the sequence of the 2B6 Vk, the original light chain partner for the 2B6 $V_H$. The light chain sequences for Fab 2 & 15 are SEQ ID NOs: 45 and 46, respectively. For Fab 2, CDRs 1–3 are SEQ ID NOs: 10, 11 and 47, respectively. For Fab 15, CDRs 1–3 are SEQ ID NOs: 10. 11 and 48, respectively.

All antibody amino acid sequences listed below in Examples 4 and 5 use the KABAT numbering system which allows variability in CDR and framework lengths. That is, key amino acids are always assigned the same number regardless of the actual number of amino acids preceding them. For example, the cysteine preceding CDR1 of all light chains is always KABAT position 23 and the tryptophan residue following CDR1 is always KABAT position 35 even though CDR1 may contain up to 17 amino acids.

EXAMPLE 4

Humanized Antibody

One humanized antibody was designed to contain murine CDRs within a human antibody framework. This humanized version of the IL-5 specific mouse antibody 2B6, was prepared by performing the following manipulations.

A. Gene Cloning:

mRNA was isolated from each of the respective 2B6, 2F2 and 2E3 hybridoma cell lines (see Example 1) with a kit obtained from Boehringer Mannheim (Indianapolis, Ind.) and then reverse transcribed using the primer (dT)$_{15}$ supplied with a cDNA kit (Boehringer Mannheim) to make cDNA. PCR primers specific for mouse immunoglobulin were used to amplify DNA coding for domains extending from amino acid #9 (KABAT numbering system) of the heavy chain variable region to the hinge region and from amino acid #9 (KABAT numbering system) of the light chain variable region to the end of the constant region. Several clones of each antibody chain were obtained by independent PCR reactions.

The mouse gamma 1 hinge region primer used is [SEQ ID NO: 22]:

5' GTACATATGCAAGGCTTACAACCACAATC 3'.

The mouse gamma 2a hinge region primer used is [SEQ ID NO: 23]:

5' GGACAGGGCTTACTAGTGGGCCCTCTGGGCTC 3'

The mouse heavy chain variable region primer used is [SEQ ID NO: 24]:

5'AGGT(C or G)(C or A)A(G or A)CT(G or T)TCTCGAGTC(T or A)GG 3'

The mouse kappa chain constant region primer used is [SEQ ID NO: 25]:

5' CTAACACTCATTCCTGTTGAAGCTCT-TGACAATGGG 3'

The mouse light chain variable region primer is [SEQ ID NO: 26]:

5' CCAGATGTGAGCTCGTGATGACCCAGACTCCA 3'

The PCR fragments were cloned into plasmids pGEM7f+ (Promega) that were then transformed into *E. coli* DH5a (Bethesda Research Labs).

B. DNA Sequencing:

The heavy and light chain murine cDNA clones from Part A above were sequenced. The results of sequencing of the variable regions of these clones are shown in SEQ ID NOs: 1–6 (FIGS. 1–6). Each clone contained amino acids known to be conserved among mouse heavy chain variable regions or light chain variable regions. The CDR amino acid sequences are listed below.

The CDR regions for the 2B6 heavy chain are SEQ ID NOs: 7, 8 and 9. See FIG. 7. These sequences are encoded by SEQ ID NO: 1. The CDR regions for the light chain are SEQ ID NOs: 10, 11 and 12. See FIG. 7. These sequences are encoded by SEQ ID NO:2.

The CDR regions for the 2F2 heavy chain are SEQ ID NOs: 7, 8 and 9. See FIG. 7. These sequences are encoded by SEQ ID NO:3. The CDR regions for the light chain are SEQ ID NOs: 10, 11 and 13. See FIG. 7. These sequences are encoded by SEQ ID NO:4.

The CDR regions for the 2E3 heavy chain are SEQ ID NOs: 7, 8 and 14. See FIG. 7. These sequences are encoded by SEQ ID NO:5. The CDR regions for the light chain are SEQ ID NOs: 10, 11 and 13. See FIG. 7. These sequences are encoded by SEQ ID NO:6.

C. Selection of Human Frameworks:

Following the cloning of 2B6, the amino acid sequences of the variable region heavy and light chains (FIGS. 1 and 2) (SEQ ID NOs: 15 and 16, respectively) were compared with the known murine immunoglobulin sequences in the KABAT and SWISS-PROT (*Nuc. Acids Res.*, 20:2019–2022 (1992)) protein sequence databases in order to assign amino acids to the N-terminal residues. The 2B6 heavy and light chain variable region deduced amino acid sequences were then compared with the human immunoglobulin protein sequence databases in order to identify a human framework for both the heavy and light chains which would most closely match the murine sequence. In addition, the heavy and light chains were evaluated with a positional database generated from structural models of the Fab domain to assess potential conflicts due to amino acids which might influence CDR presentation. Conflicts were resolved during synthesis of the humanized variable region frameworks by substitution of the corresponding mouse amino acid at that location.

The heavy chain framework regions of an antibody obtained from a human myeloma immunoglobulin (COR) was used (E. M. Press and N. M. Hogg, *Biochem. J.*, 117:641–660 (1970)). The human heavy chain framework amino acid sequence was found to be approximately 66% homologous to the 2B6 framework.

For a suitable light chain variable region framework, the light chain variable framework sequence of the Bence-Jones protein, (LEN) (Schneider et al., *Hoppe-Seyler's Z. Physiol. Chem.*, 356:507–557 (1975)), was used. The human light chain framework regions were approximately 82% homologous to the murine 2B6 light chain framework regions, at the amino acid level.

The selected human frameworks were back translated to provide a DNA sequence.

D. Construction of Humanized MAb Genes:

Given the 2B6 heavy chain CDRs [FIG. 7 and SEQ ID NOs: 1–2] and the framework sequences of the human antibodies, a synthetic heavy chain variable region was made [SEQ ID NO: 18]. This was made using four synthetic oligonucleotides [SEQ ID NOs:27 and 28] [SEQ ID NOs: 29 and 30] which, when joined, coded for amino acids #21–#106 (KABAT numeration). The oligonucleotides were then ligated into the HpaI-KpnI restriction sites of a pUC 18 based plasmid containing sequences derived from another humanized heavy chain based on the COR framework (supra). This plasmid provides a signal sequence [SEQ ID NO: 17] and the remaining variable region sequence. Any errors in the mapped sequence were corrected by PCR with mutagenic primers or by the addition of synthetic linkers into existing restriction sites.

The signal sequence and humanized heavy chain variable region were excised from the pUC based plasmid as a EcoRI-ApaI fragment and ligated into the expression vector pCD that contained an $IgG_1$ human constant region. The synthetic heavy chain variable region nucleotide and amino acid sequences are provided in FIG. 8 [SEQ ID NOs: 18 and 19]. The human framework residues are amino acids 1–30, 36–49, 66–97 and 109–119 of SEQ ID NO: 19. The amino acid sequences of the CDRs are identical to the murine 2B6 CDRs. The resulting expression vector, pCDIL5HZHC1.0, is shown in FIG. 10.

Given the 2B6 light chain CDRs [FIG. 7 and SEQ ID NOs: 10, 11 and 12] and the framework sequence of the human antibody, a synthetic light chain variable region was made [SEQ ID NO: 20]. Four synthetic oligonucleotides coding for amino acids #27–#58 (KABAT numeration)[SEQ ID NOs:31 and 32] and amino acids #80–#109 [SEQ ID NOs:33 and 34] of the humanized $V_L$ with SacI-KpnI and PstI-HindIII ends respectively, were inserted into a pUC18 based plasmid containing sequences derived from another human light chain framework (B17) (Marsh et al, *Nuc. Acids Res.*, 13:6531–6544 (1985)) which shares a high degree of homology to the LEN framework. This plasmid provides the remaining variable region sequence. Any errors in the mapped sequence and the single amino acid difference between the LEN and B17 frameworks were corrected by PCR with mutagenic primers or by the addition of synthetic linkers into existing restriction sites.

The humanized light chain variable region was isolated from the pUC plasmid as a EcoRV-NarI fragment and ligated into the expression vector pCN that contained a signal sequence [SEQ ID NO: 17] along with a kappa human constant region. The synthetic light chain variable region nucleotide and amino acid sequences are provided in FIG. 9 [SEQ ID NOs:20 and 21]. The human framework residues are amino acids 1–23, 41–55, 63–94 and 104–113 of SEQ ID NO: 21. The amino acid sequences of the CDRs are identical to the murine 2B6 CDRs. However, the coding sequences for these CDRs differ from the murine 2B6 coding sequences to allow creation of restriction enzyme sites. One of the resulting expression vectors, pCNIL5HZLC1.0, is shown in FIG. 1. These synthetic variable light and/or heavy chain sequences are employed in the construction of a humanized antibody.

E. Expression of Humanized MAb:

The humanized heavy chain, derived from an $IgG_1$ isotype, utilizes a synthetic heavy chain variable region as provided in SEQ ID NO:19. This synthetic $V_H$ containing the 2B6 heavy chain CDRs was designed and synthesized as described above.

Figure 11:
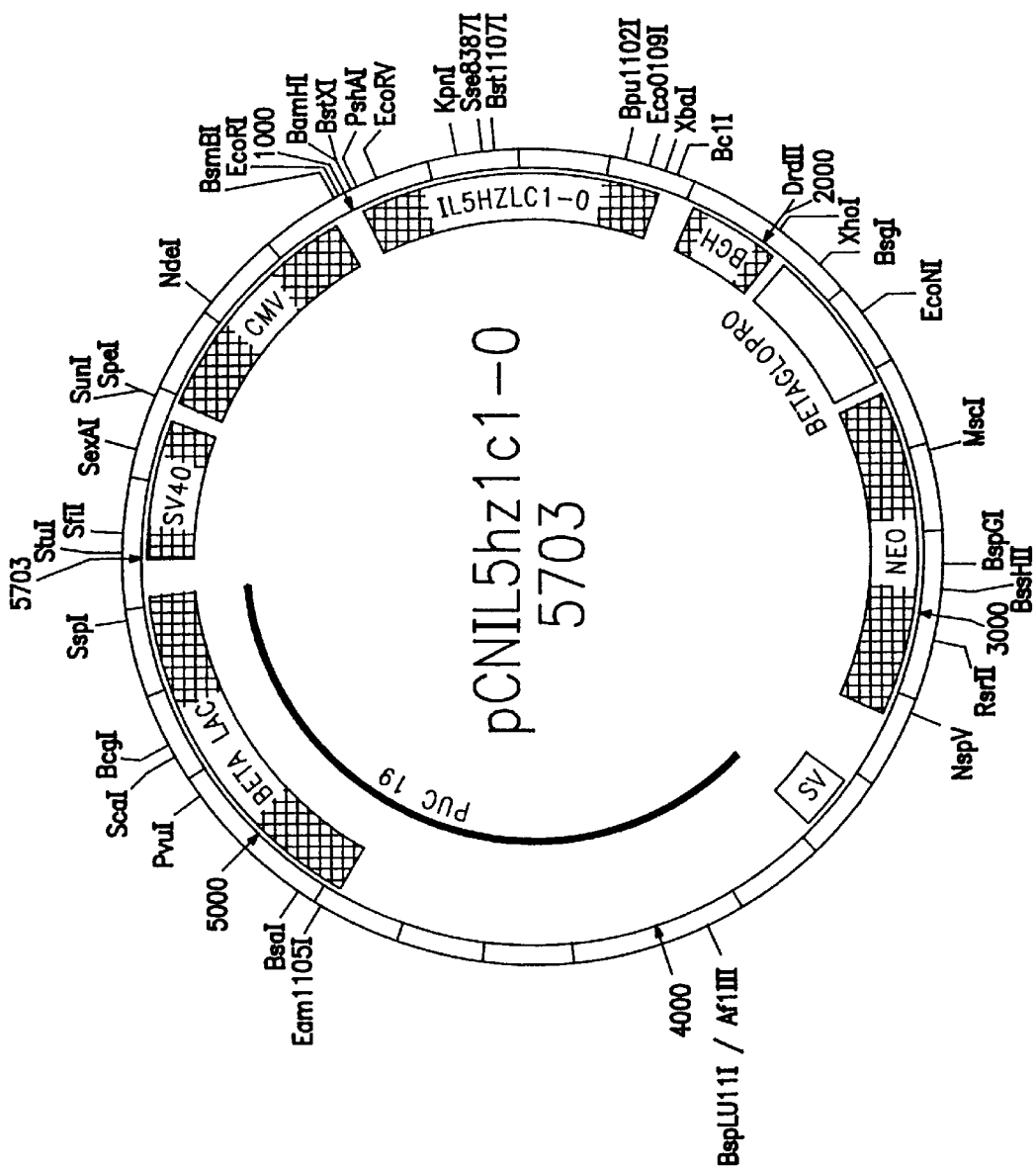
FIG. 11 is a schematic drawing of plasmid pCNIL5HZLC1.0 employed to express a humanized light chain gene in mammalian cells.

The humanized light chain, a human kappa chain, utilizes a synthetic light chain variable region as provided in SEQ ID NO: 21. This synthetic $V_L$ containing the 2B6 light chain CDRs was designed and synthesized as described above. The DNA fragments coding for the humanized variable regions were inserted into pUC19-based mammalian cell expression plasmids that utilize a signal sequence and contain CMV promoters and the human heavy chain or human light chain constant regions of the chimera produced in Example 5 below, by conventional methods (Maniatis et al., cited above) to yield the plasmids pCDIL5HZHC1.0 (heavy chain) [SEQ ID NO: 49, see also FIG. 10] and pCNIL5HZLC1.0 (light chain) [SEQ ID NO: 50, see also FIG. 11]. The plasmids were co-transfected into COS cells and supernatants assayed after three and five days, respectively, by the ELISA described in Example 5 for the presence of human antibody.

The above example describes the preparation of an exemplary engineered antibody. Similar procedures may be followed for the development of other engineered antibodies, using other anti-IL-5 antibodies (e.g., 2F2, 2E3, 4A6, 5D3, 24G9, etc.) developed by conventional means.

F. Purification:

Purification of CHO expressed chimeric and humanized 2B6 can be achieved by conventional protein A (or G) affinity chromatography followed by ion exchange and molecular sieve chromatography. Similar processes have been successfully employed for the purification to >95% purity of other mAbs (e.g., to respiratory syncytial virus, interleukin-4 and malaria circumsporozoite antigens).

G. Additional Humanized mAbs and Expression Plasmids:

Given the plasmid pCDIL5HZHC1.0 [SEQ ID NO: 49] the expression plasmid pCDIL5HZHC1.1 was made that substitutes an Asparagine for Threonine at framework position 73. This was done by ligating a synthetic linker with EcoRV and XhoI ends [SEQ ID NO: 51 and SEQ ID NO: 52] into identically digested pCDIL5HZHC1.0. Similarly, the expression plasmid pCDIL5HZHC1.2 substitutes an Isoleucine for Valine at framework position 37. This was accomplished by ligating a synthetic linker with HpaI and XbaI ends [SEQ ID NO: 53 and SEQ ID NO: 54] into identically digested pCDIL5HZHC1.0 1. 0. The expression plasmid pCDIL5HZHC1.0 1. 3 was also made by ligating a synthetic linker with HpaI and XbaI ends [SEQ ID NO: 53 and SEQ ID NO: 54] into identically digested pCDIL5HZHC1.1.

Given the pUC 18 based plasmid described previously which contains DNA sequences of four synthetic oligonucleotides [SEQ ID NOs: 31, 32, 33 and 34], a humanized light chain variable region was made where framework position #15 is changed from a Leucine to Alanine. This plasmid was digested with NheI and SacI restriction endonucleases and a synthetic linker [SEQ ID NOs: 55 and 56] was inserted. An EcoRV-NarI fragment was then isolated and ligated into the identically digested expression vector pCNIL5HZLC1.0 to create pCNIL5HZLC1.1.

A synthetic variable region was made using the heavy chain framework regions obtained from immunoglobulin (NEW) (Saul et al, *J. Biol. Chem.* 253:585–597(1978)) and the 2B6 heavy chain CDRs [FIG. 7 and SEQ ID NOs: 1–2]. Framework amino acids which might influence CDR presentation were identified and substitutions made using methods described previously. Four overlapping synthetic oligonucleotides were generated [SEQ ID NOs: 57, 58, 59 and 60] which, when annealed and extended, code for amino acids representing a signal sequence [SEQ ID NO: 17] and a heavy chain variable region. This synthetic gene was then amplified using PCR primers [SEQ ID NOs: 63 and 64] and ligated as a BstXI-HindIII restriction fragment into a pUC 18 based plasmid containing sequences derived from another humanized heavy chain based on the COR framework. A phenylalanine to tyrosine framework substitution was made at amino acid position 91 (Kabat numbering system) (equivalent to position 94 of FIG. 12) by inserting a synthetic oligonucleotide linker [SEQ ID NOs: 75 and 76] into SacII and KpnI restriction sites. The resulting heavy chain variable region [FIG. 12 and SEQ ID NOs: 61, 62] is referred to as the NEWM humanized heavy chain.

Any errors in the mapped sequence were corrected by PCR with mutagenic primers or by the addition of synthetic linkers into existing restriction sites. The signal sequence and humanized heavy chain variable region were excised from the pUC based plasmid as a EcoRI-ApaI fragment and ligated into the expression vector pCD that contained a human IgG$_1$ constant region to create the plasmid pCDIL5NEWM. The amino acid sequences of the CDRs are identical to the murine 2B6 heavy chain CDRs.

A synthetic variable region was made using the light chain framework regions obtained from immunoglobulin (REI) (Palm et al, *Hoppe-Seyler's Z. Physiol. Chem.* 356:167–191 (1975)) and the 2B6 light chain CDRs [FIG. 7 and SEQ ID NOs: 10, 11 and 12]. Framework amino acids which might influence CDR presentation were identified and substitutions made using methods described previously. Four overlapping synthetic oligonucleotides were generated [SEQ ID NOs: 65, 66, 67 and 68] which, when annealed and extended, code for amino acids representing a light chain variable region [FIG. 13 and SEQ ID NOs: 69, 70] referred to as the REI humanized light chain. This synthetic gene was then amplified using PCR primers [SEQ ID NOs: 71 and 72] and ligated as an EcoRI-HindIII restriction fragment into pGEM-7Zf(+) (Promega Corporation, Madison, Wis.).

Any errors in the mapped sequence were corrected by PCR with mutagenic primers or by the addition of synthetic linkers into existing restriction sites. The humanized light chain variable region was excised from the pGEM-7Zf(+) based plasmid as an EcoRV-NarI fragment and ligated into the expression vector pCN that contained a signal sequence [SEQ ID NO: 17] along with a human Kappa constant region to create the plasmid pCNIL5REI. The amino acid sequences of the CDRs are identical to the murine 2B6 light chain CDRs. However, the coding sequences for these CDRs differ from the murine 2B6 coding sequences to allow creation of restriction enzyme sites. These synthetic variable light and/or heavy chain sequences are employed in the construction of a humanized antibody.

Given the pGEM-7Zf(+) based plasmid described above, a humanized light chain variable region can be made where framework position #15 is changed from a Valine to Alanine. This plasmid may be digested with NheI and SacI restriction endonucleases and a synthetic linker [SEQ ID NOs: 73 and 74] is inserted. An EcoRV-NarI fragment may then be isolated and ligated into the identically digested expression vector pCNIL5HZREI to create the plasmid pCNL5REI$_{V15A}$.

EXAMPLE 5

Construction of a Chimeric Antibody

DNA coding for amino acids #9–#104 (KABAT numeration) of the murine mAb 2B6 heavy chain variable region was isolated as a AvaII-StyI restriction fragment from a pGEM7Zf+ based PCR clone of cDNA generated from the 2B6 hybridoma cell line (see Example 4). The flanking heavy chain variable region sequences and a signal sequence [SEQ ID NO: 17] were provided by combining this fragment along with four small synthetic oligomer linkers [SEQ ID NOs: 35 and 36] [SEQ ID NOs: 37 and 38] into a pUC18 based plasmid digested with BstX1-HindIII. A consensus of N-terminal amino acids deduced from closely related murine heavy chains were assigned for the first eight V$_H$ residues and are coded within SEQ ID NOs: 35 and 36. The deduced amino acid sequence of the heavy chain was verified by the sequencing of the first 15 N-terminal amino acids of the 2B6 heavy chain.

An EcoRI-ApaI fragment containing sequence for signal and V$_H$ regions was isolated and ligated into plasmid pCD that already encodes the human IgG1 constant region.

DNA coding for amino acids #12–#99 (KABAT nomenclature) of the murine mAb 2B6 light chain variable region was isolated as a DdeI-AvaI restriction fragment from a pGEM7Zf+based PCR clone of cDNA generated from the 2B6 hybridoma cell line (see Example 4). The flanking light chain variable region sequences were provided by combining this fragment along with four small synthetic oligomer linkers [SEQ ID NOs: 39 and 40] [SEQ ID NOs: 41 and 42] into a pUC 18 based plasmid digested with EcoRV-HindIII. A consensus of N-terminal amino acids deduced from closely related murine light chains were assigned for the first eight $V_L$ residues and are coded within SEQ ID NOs: 39 and 40. The deduced amino acid sequence of the light chain was verified by the sequencing of the first 15 N-terminal amino acids of the 2B6 light chain. This variable region was then isolated as a EcoRV-NarI fragment and ligated into the expression vector pCN that already contains the human kappa region and a signal sequence.

Expression of a chimeric antibody was accomplished by co-transfection of the pCD and pCN based plasmids into COS cells. Culture supernatants were collected three and five days later and assayed for immunoglobulin expression by ELISA described as follows: Each step except for the last is followed by PBS washes. Microtiter plates were coated overnight with 100 ng/50 ul/well of a goat antibody specific for the Fc region of human antibodies. The culture supernatants were added and incubated for 1 hour. Horseradish peroxidase conjugated goat anti-human IgG antibody was then added and allowed to incubate for 1 hour. This was followed by addition of ABTS peroxidase substrate (Kirkegaard & Perry Laboratories Inc., Gaithersburg, Md.). After 1 hour incubation, the absorbance at 405 nm was read on a microtiter plate reader (Molecular Devices Corporation, Menlo Park, Calif.). Expression of the chimeric antibody was detected. In a similar ELISA, the COS cell supernatants, containing the chimeric antibody, bound specifically to microtiter wells coated with human IL-5 protein. This result confirmed that genes coding for an antibody to IL-5 had been synthesized and expressed.

The above example describes the preparation of an exemplary engineered antibody. Similar procedures may be followed for the development of other engineered antibodies, using other anti-IL-5 donor antibodies (e.g., 2F2, 2E3, 4A6, 5D3, 24G9, etc.) developed by conventional means.

What is claimed is:

1. A method of treating conditions associated with excess eosinophil production in a human comprising the step of administering to said human in need thereof an effective amount of an altered antibody having the affinity and neutralizing activity of a monoclonal antibody produced by a hybridoma cell line having ATCC Accession Number HB 11783, HB 11782, HB 11781 or HB 11943.

2. The method of claim 1 wherein the altered antibody has the affinity and neutralizing activity of a monoclonal antibody produced by a hybridoma cell line having ATCC Accession Number HB 11783.

3. The method of claim 1 wherein the altered antibody has the affinity and neutralizing activity of a monoclonal antibody produced by a hybridoma cell line having ATCC Accession Number HB 11782.

4. The method of claim 1 wherein the altered antibody has the affinity and neutralizing activity of a monoclonal antibody produced by a hybridoma cell line having ATCC Accession Number HB 11781.

5. The method of claim 1 wherein the altered antibody has the affinity and neutralizing activity of a monoclonal antibody produced by a hybridoma cell line having ATCC Accession Number HB 11943.

6. The method of claim 1 wherein the condition is asthma.

7. The method of claim 1 wherein the condition is allergic rhinitis.

8. The method of claim 1 wherein the condition is atopic dermatitis.

* * * * *